US007915298B2

(12) United States Patent
Gosselin et al.

(10) Patent No.: US 7,915,298 B2
(45) Date of Patent: Mar. 29, 2011

(54) COMPOUNDS AND METHODS FOR LEUKOTRIENE BIOSYNTHESIS INHIBITION

(75) Inventors: Francis Gosselin, Jersey City, NJ (US); Vicky Vydra, Tinton Falls, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 139 days.

(21) Appl. No.: 12/284,665

(22) Filed: Sep. 24, 2008

(65) Prior Publication Data

US 2009/0088477 A1 Apr. 2, 2009

Related U.S. Application Data

(60) Provisional application No. 60/995,525, filed on Sep. 27, 2007.

(51) Int. Cl.

| | |
|---|---|
| ***A61K 31/42*** | (2006.01) |
| ***A61K 31/352*** | (2006.01) |
| ***C07D 271/113*** | (2006.01) |
| ***C07D 311/06*** | (2006.01) |

(52) U.S. Cl. ......... 514/364; 514/456; 548/143; 549/399

(58) Field of Classification Search .................. 514/576, 514/364, 456; 562/45; 548/143; 549/399
See application file for complete search history.

(56) References Cited

U.S. PATENT DOCUMENTS

| | | | | |
|---|---|---|---|---|
| 5,424,320 | A | 6/1995 | Fortin et al. | |
| 7,553,973 | B2 * | 6/2009 | Blouin et al. | 548/128 |
| 2009/0030048 | A1 * | 1/2009 | Blouin et al. | 514/363 |
| 2009/0227638 | A1 * | 9/2009 | Blouin et al. | 514/363 |

FOREIGN PATENT DOCUMENTS

| | | | |
|---|---|---|---|
| WO | WO2004/108720 | A1 | 12/2004 |
| WO | WO2006/099735 | A1 | 9/2006 |
| WO | WO 2006099736 | A1 * | 9/2006 |
| WO | WO2007/038865 | A1 | 4/2007 |

* cited by examiner

*Primary Examiner* — Yong Chu
(74) *Attorney, Agent, or Firm* — Mollie M. Yang; Valerie J. Camara

(57) ABSTRACT

This invention provides novel salt and crystalline forms thereof of (−)4-(4-fluorophenyl)-7-[({5-[1-hydroxy-1-(trifluoromethyl)propyl]-1,3,4-oxadiazol-2-yl}amino)-methyl]-2H-chromen-2-one. The compounds are 5-LO inhibitors and are useful for treatment of conditions such as asthma, allergic rhinitis, COPD, and atherosclerosis.

6 Claims, 10 Drawing Sheets

COMPOUNDS AND METHODS FOR LEUKOTRIENE BIOSYNTHESIS INHIBITION

CROSS REFERENCE TO RELATED APPLICATION

This application claims priority from U.S. Provisional Application Ser. No. 60/995,525, filed Sep. 27, 2007.

BACKGROUND OF THE INVENTION

The instant invention relates to novel salt forms and crystalline forms thereof of (S)4-(4-fluorophenyl)-7-[({5-[1-hydroxy-1-(trifluoromethyl)propyl]-1,3,4-oxadiazol-2-yl}amino)methyl]-2H-chromen-2-one, and its use as a leukotriene biosynthesis inhibitor alone or in combination with other active agents to treat conditions such as asthma, allergic rhinitis, chronic obstructive pulmonary disease and atherosclerosis.

Inhibition of leukotriene biosynthesis has been an active area of pharmaceutical research for many years. The leukotrienes constitute a group of locally acting hormones, produced in living systems from arachidonic acid. Leukotrienes are potent contractile and inflammatory mediators derived by enzymatic oxygenation of arachidonic acid by 5-lipoxygenase. One class of leukotriene biosynthesis inhibitors are those known to act through inhibition of 5-lipoxygenase (5-LO).

The major leukotrienes are Leukotriene $B_4$ (abbreviated as $LTB_4$), $LTC_4$, $LTD_4$ and $LTE_4$. The biosynthesis of these leukotrienes begins with the action of the enzyme 5-lipoxygenases on arachidonic acid to produce the epoxide known as Leukotriene $A_4$ ($LTA_4$), which is converted to the other leukotrienes by subsequent enzymatic steps. Further details of the biosynthesis as well as the metabolism of the leukotrienes are to be found in the book Leukotrienes and Lipoxygenases, ed. J. Rokach, Elsevier, Amsterdam (1989). The actions of the leukotrienes in living systems and their contribution to various diseases states are also discussed in the book by Rokach.

In general, 5-LO inhibitors have been sought for the treatment of allergic rhinitis, asthma and inflammatory conditions including arthritis. One example of a 5-LO inhibitor is the marketed drug zileuton (ZYLOFT®) which is indicated for the treatment of asthma. More recently, it has been reported that 5-LO may be an important contributor to the atherogenic process; see Mehrabian, M. et al., Circulation Research, Jul. 26, 2002 91(2):120-126.

The compound 4-(4-fluorophenyl)-7-[({5-[1-hydroxy-1-(trifluoromethyl)propyl]-1,3,4-oxadiazol-2-yl}amino)methyl]-2H-chromen-2-one, including the (−) and (+) enantiomer species thereof and pharmaceutically acceptable salts thereof, is presented in PCT application number CA2006/000432, having publication number WO2006/099735. The instant invention provides novel salts of (−)4-(4-fluorophenyl)-7-[({5-[1-hydroxy-1-(trifluoromethyl)propyl]-1,3,4-oxadiazol-2-yl}amino)methyl]-2H-chromen-2-one and crystalline forms thereof which have advantageous properties for use as a pharmaceutical drug.

SUMMARY OF THE INVENTION

Figure 1:
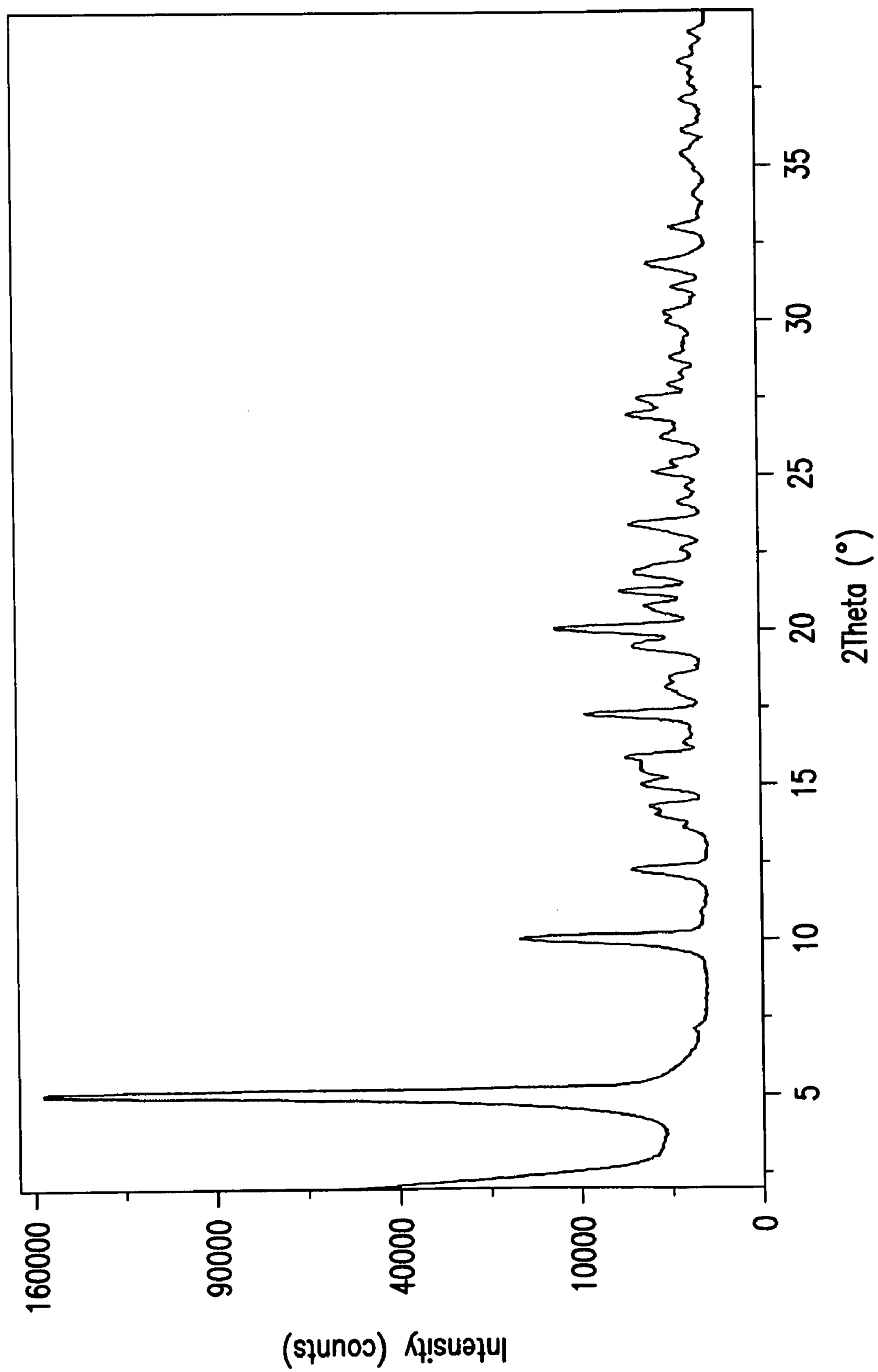
FIG. 1 is a characteristic X-ray diffraction pattern (XRPD) of the anhydrous crystalline Compound I tosylate salt, Form A.

The structure of free-base compound (−)4-(4-fluorophenyl)-7-[({5-[1-hydroxy-1-(trifluoromethyl)propyl]-1,3,4-oxadiazol-2-yl}amino)methyl]-2H-chromen-2-one is shown below:

Compound I

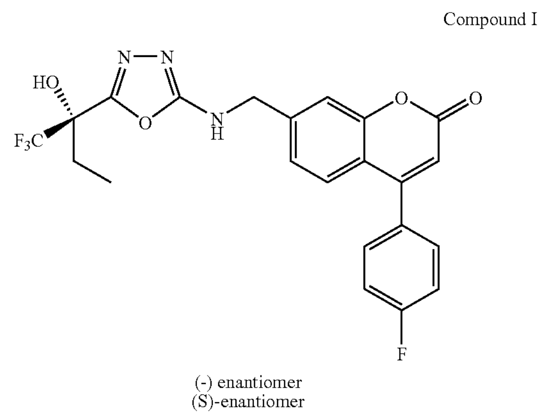

(-) enantiomer
(S)-enantiomer

The absolute configuration of (−)4-(4-fluorophenyl)-7-[({5-[1-hydroxy-1-(trifluoromethyl)-propyl]-1,3,4-oxadiazol-2-yl}amino)methyl]-2H-chromen-2-one is (S) and therefore this compound is also identified as (S)-4-(4-fluorophenyl)-7-[({5-[1-hydroxy-1-(trifluoromethyl)-propyl]-1,3,4-oxadiazol-2-yl}amino)methyl]-2H-chromen-2-one. For brevity, the compound (S)-4-(4-fluorophenyl)-7-[({5-[1-hydroxy-1-(trifluoromethyl)propyl]-1,3,4-oxadiazol-2-}amino)-methyl]-2H-chromen-2-one (the free base) is also referred to herein as "Compound I."

One object of the instant invention is to provide novel besylate and tosylate salts of the 5-LO inhibitor (S)-4-(4-fluorophenyl)-7-[({5-[1-hydroxy-1-(trifluoromethyl)propyl]-1,3,4-oxadiazol-2-yl}amino)methyl]-2H-chromen-2-one. Another object is to provide the novel anhydrous crystalline (S)-4-(4-fluorophenyl)-7-[({5-[1-hydroxy-1-(trifluoromethyl)propyl]-1,3,4-oxadiazol-2-yl}amino)methyl]-2H-chromen-2-one tosylate salt as well as solvated forms thereof. The invention also provides pharmaceutical compositions containing these salts.

Another object of the instant invention is to provide a method for preventing the synthesis, the action, or the release of leukotrienes, and for treating inflammatory conditions, which comprises administering to a host in need thereof an effective amount of a salt of the present invention.

The instant invention further provides methods of preventing or treating asthma, allergic rhinitis or chronic obstructive pulmonary disease comprising administering a therapeutically effective amount of a salt of this invention to a patient in need of the above-described treatments.

Additionally, the salts of this invention are useful as pharmaceutical agents to slow or halt atherogenesis. Therefore, the instant invention provides a method for treating atherosclerosis, which includes halting or slowing the progression of atherosclerotic disease once it has become clinically evident, comprising administering a therapeutically effective amount of a salt of this invention to a patient in need of such treatment. The instant invention also provides methods for preventing or reducing the risk for having an atherosclerotic disease event, comprising administering a prophylactically effective amount of a salt of this invention to a patient who is at risk of developing atherosclerosis or having an atherosclerotic disease event.

The instant invention further provides the use of a salt of this invention in combination with other therapeutically effective agents. Additional embodiments will be evident from the following detailed description.

DETAILED DESCRIPTION OF THE INVENTION

Compound I is a pharmacologically active free-base compound. The salts of the present invention can be prepared by combining free-base Compound I with either benzene-sulfonic or p-toluenesulfonic acid to provide the besylate and tosylate salts, respectively. Compound I tosylate salt is preferred. For the purpose of clarity, the following salt names can be used interchangeably and have the same meaning: the p-toluenesulfonic acid salt of Compound I can also be referred to as the p-toluenesulfonate, 4-methylphenylsulfonate or tosylate salt of Compound I; and the benzenesulfonic acid salt of Compound I can also be referred to as the benzenesulfonate or besylate salt of Compound I.

The salts of Compound I may be prepared by placing Compound I free base in contact with the appropriate acid in an organic solvent such as 1,2-dichloroethane, isopropyl acetate (iPAc), ethyl acetate, tetrahydrofuran, heptane, methylcyclohexane, acetonitrile, acetone, as well as nitromethane, cyclohexane, i-propyl alcohol and methyl isobutyl ketone, heating, if needed, up to reflux to obtain a solution followed by cooling to induce precipitation. The salt in solid form may precipitate from a single solvent or precipitation may be initiated by addition of an anti solvent and can be collected by filtration.

The tosylate salt of Compound I readily forms solvates with organic solvents, for example but not limited to iPAc, heptane, methylcyclohexane, tetrahydrofuran, acetonitrile and acetone, as well as nitromethane, cyclohexane, i-propyl alcohol and methyl isobutyl ketone (MIBK). Such solvates can be formed by combining anhydrous crystalline form of the tosylate salt of Compound I (hereinafter referred to as Form A) with an organic solvent and stirring to form a slurry. Conversion from an anhydrous form to a solvated form can occur over varying timeframes, for example from a few hours to several days, and can be monitored by known analytical techniques such as XRPD. Analysis to detect the formation of a solvate can be performed on a sample of the slurry, or the slurry can be filtered and the analysis performed on the resulting wet cake. If the analysis is performed on the wet cake, it must be done in sufficient time prior to evaporation/desolvation of the solvent from the crystalline compound.

Solvated Compound I tosylate salt readily desolvates to the anhydrous Form A. Desolvation can be accomplished by standard methods known in the art, for example by allowing the solvated compound to sit in an open container at ambient temperature (i.e., about 25° C.) until the solvent evaporates, or by accelerating evaporation of the solvent using elevated temperatures and/or vacuum.

Crystalline solvates of Compound I tosylate salt as described herein are those solvated crystal forms which, when desolvated, result in anhydrous crystalline Form A. Since such crystalline solvates are the solvated counterparts to crystalline anhydrous Form A, the solvated crystal forms may share certain physical characteristic data with Form A, where the data is derived from solid state analysis. For example, crystalline solvates of Compound I tosylate salt and anhydrous Form A may share one or more of the same or reasonably similar d-spacings in their XRPD, or the same or reasonably similar chemical shifts in the solid-state carbon-13 CPMAS NMR spectra. Accordingly, such solvates are within the scope of this invention.

The amorphous tosylate salt of Compound I can be generated by milling, spray drying or melt-quenching of the crystalline tosylate salt. The amorphous tosylate salt can be re-crystallized to crystalline tosylate salt in an organic solvent such as 1,2-dichloroethane, isopropyl acetate ethyl acetate, tetrahydrofuran, heptane, methylcyclohexane, acetonitrile, acetone, as well as nitromethane, cyclohexane, i-propyl alcohol and methyl isobutyl ketone, heating, if needed, up to reflux to obtain a solution followed by cooling to induce precipitation. Re-crystallization can be accelerated at elevated relative humidity and/or elevated temperature. For example, heating the amorphous material to greater than 100° C. and holding it isothermal till re-crystallization completion is detected by analytical techniques such as MDSC or XRPD.

Besylate salt. The besylate salt of Compound I can be characterized by proton magnetic resonance spectrum as follows: $^1$H NMR (DMSO-$d_6$, 400.1 MHz) δ8.56 (t, J=6.0 Hz, 1H), 7.63-7.58 (overlapping m, 4H), 7.44-7.38 (overlapping m, 4H), 7.35-7.30 (overlapping m, 4H), 6.42 (s, 1H), 4.52 (d, J=6.0 Hz, 2H), 2.14-2.05 (m, 1H), 2.02-1.93 (m, 1H), 0.89 (t, J=7.2 Hz, 3H).

Figure 10:
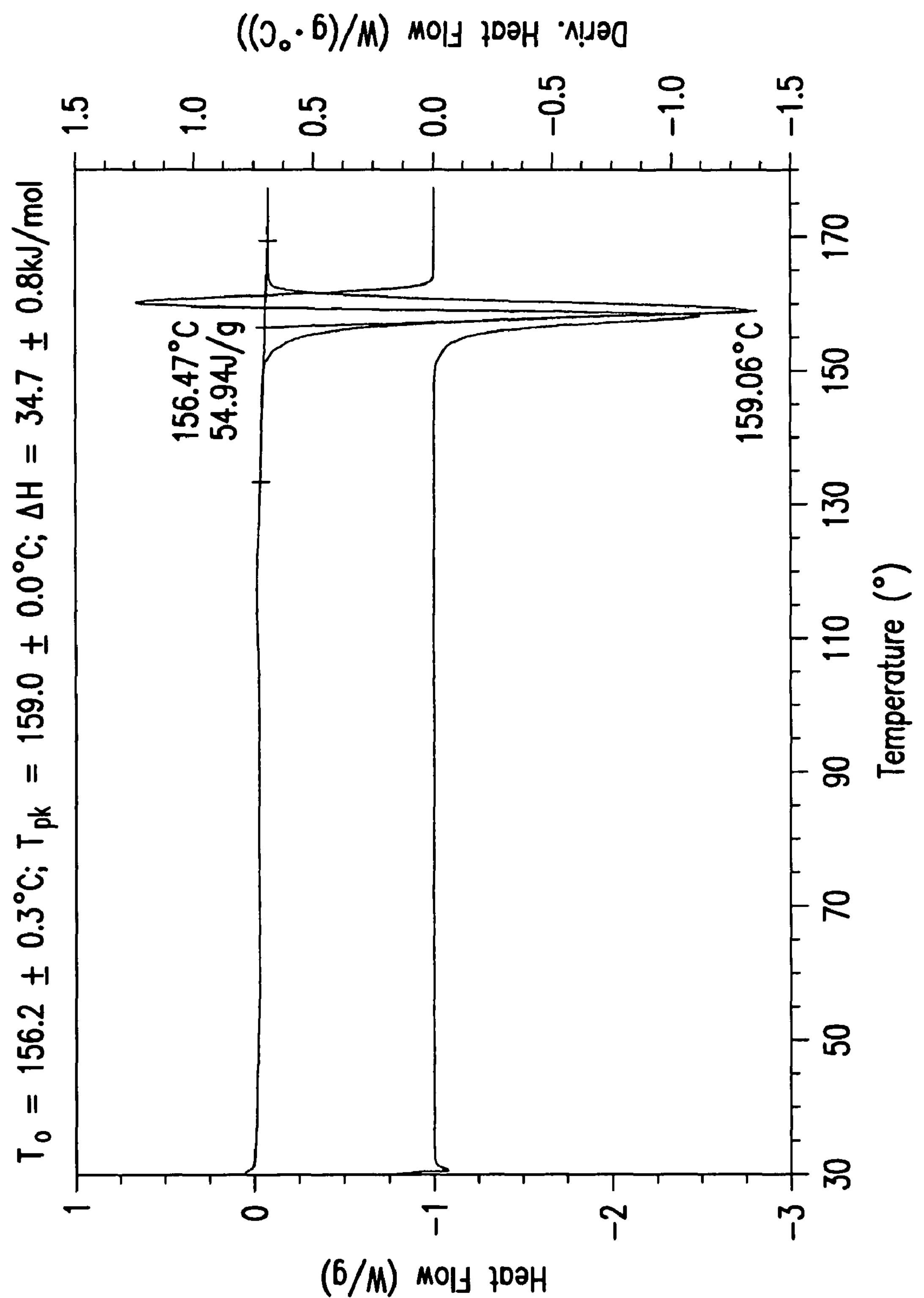
FIG. 10 is a typical differential scanning calorimetry (DSC) curve of the crystalline Compound I besylate salt.

The besylate salt is also characterized by differential scanning calorimeter (DSC). The data were acquired using a TA robotic DSC (Q1000). DSC analyses (n=2) were carried out in crimped aluminium pans (10° C./min, 50 mL/min nitrogen). The DSC was calibrated for temperature and heat flow with indium (Goodfellow, 99.999% Pure), and tin (NIST SRM 2220). FIG. 10 shows the differential calorimetry scan for the crystalline besylate salt. The DSC curve shows an onset melting temperature of 156° C. (peak temperature of 159° C.).

XRPD patterns were measured using a Scintag XDS-2000, Si(Li) Peltier-cooled solid state detector, CuKα source using a generator power of 45 kV and current of 40 mA. A divergent beam of 2 mm and 4 mm and receiving beam slits of 0.5 mm and 0.2 mm were used. Scan range was set from 2-50°2θ in step mode using a step size of 0.02° and a 2 second count time per step. The sample was measured on a quartz disk. Peak positions were verified using a standard corundum plate (NIST SRM 1976).

Figure 9:
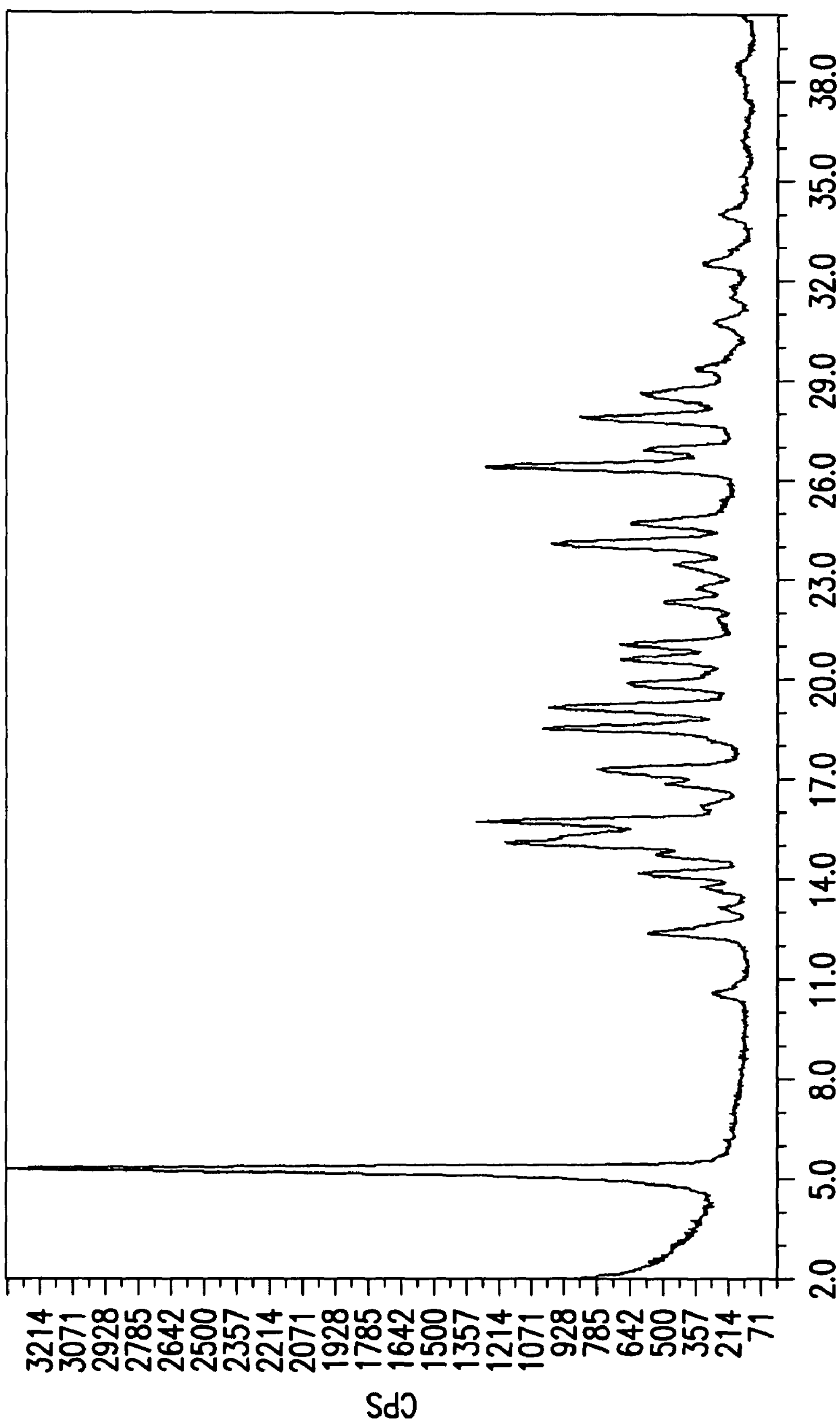
FIG. 9 is a characteristic X-ray diffraction pattern (XRPD) of the crystalline Compound I besylate salt.

FIG. 9 shows the X-ray powder diffraction pattern of the crystalline besylate salt of Compound I. The besylate salt has characteristic diffraction peaks corresponding to d-spacings of 27.89, 26.46, 24.15, 19.24, 18.62, 17.34, 15.78, 15.13, 5.35 angstroms. In particular, the besylate salt can be characterized by having an XRPD pattern obtained using CuKα radiation containing at least one diffraction peak corresponding to a d-spacing selected from the group consisting of 27.89, 26.46, 24.15, 19.24, 18.62, 17.34, 15.78, 15.13, 5.35 angstroms. More particularly, the besylate salt can be characterized by having an XRPD pattern obtained using CuKα radiation containing at least two diffraction peaks corresponding to d-spacings selected from the group consisting of 27.89, 26.46, 24.15, 19.24, 18.62, 17.34, 15.78, 15.13, 5.35 angstroms. Even more particularly, the besylate salt can be characterized by having an XRPD pattern obtained using CuKα radiation containing at least three diffraction peaks corresponding to d-spacings selected from the group consisting of 27.89, 26.46, 24.15, 19.24, 18.62, 17.34, 15.78, 15.13, 5.35 angstroms.

The crystalline besylate salt of Compound I can also be characterized by the X-ray diffraction pattern of FIG. 9.

Tosylate salt. A proton magnetic resonance spectrum of the tosylate salt of Compound I was obtained using a Bruker DRX-600 nuclear magnetic resonance (NMR) spectrometer operating at a frequency of 600.13 MHz. The sample concentration was approximately 4.4% (w/v) in $CD_3OD$. The reference compound was $CD_2HOD$ (3.31 ppm). Signal assignments are tabulated following the numbered structural formula of the tosylate salt of Compound I shown below.

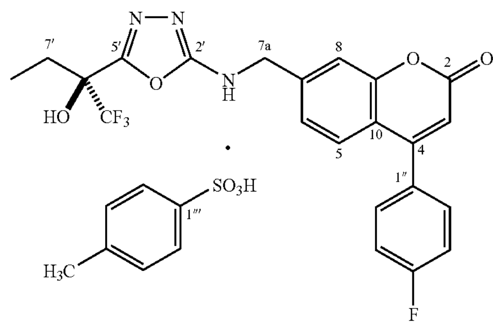

| $\delta_H$ (ppm) | Multiplicity[1] | Assignment[2,3] |
|---|---|---|
| 7.68 | m | $C_{2'''}H$, $C_{6'''}H$ |
| 7.54 | m | $C_{2''}H$, $C_{6''}H$ |
| 7.51 | d, J = 8.2 | $C_5H$ |
| 7.50 | d, J = 1.6 | $C_8H$ |
| 7.36 | dd, J = 8.2, 1.6 | $C_6H$ |
| 7.31 | m | $C_{3''}H$, $C_{5''}H$ |
| 7.21 | d, J = 8.0 | $C_{3'''}H$, $C_{5'''}H$ |
| 6.38 | s | $C_3H$ |
| 4.71 | s | $C_{7a}H_2$ |
| 2.35 | s | Tosyl $CH_3$ |
| 2.21, 2.11 | m (x2) | $C_{7'}H_2$ |
| 1.02 | t, J = 7.4 | $C_{8'}H_3$ |

[1]Multiplicity: s = singlet, d = doublet, t = triplet, m = multiplet; coupling constants (J) in hertz.
[2]The resonance at 4.90 ppm is due to actives.
[3]A trace of isopropylacetate is observed.

The X-ray powder diffraction patterns of Form A and the crystalline iPAc (i-propyl acetate) solvate of the tosylate salt of Compound I were generated on a Philips Analytical X'Pert PRO X-ray Diffraction System with PW3040/60 console. A PW3373/00 ceramic Cu LEF X-ray tube K-Alpha radiation was used as the source (wavelength=1.54 angstroms).

In addition to the X-ray powder diffraction studies described above, Form A and the crystalline iPAc solvate of the tosylate salt of Compound I were also characterized by solid-state carbon-13 nuclear magnetic resonance (NMR) spectra. The solid-state carbon-13 NMR spectra were obtained on a Bruker DSX 500 WB NMR system using a Bruker 4 mm H/X/Y CPMAS probe. The carbon-13 NMR spectra utilized proton/carbon-13 cross-polarization magic-angle spinning with variable-amplitude cross polarization, total sideband suppression, and SPINAL decoupling at 100 kHz. The samples were spun at 10.0 kHz, and a total of 20480 scans were collected with a recycle delay of 3 seconds. A line broadening of 10 Hz was applied to the spectra before FT was performed. Chemical shifts are reported on the TMS scale using the carbonyl carbon of glycine (176.03 p.p.m.) as a secondary reference.

Form A was also characterized by solid state fluorine-19 NMR. The solid-state fluorine-19 NMR spectra were obtained on a Bruker DSX 500WB NMR system using a Bruker 4 mm H/F/X CPMAS probe. The fluorine-19 NMR spectra utilized proton/fluorine-19 cross-polarization magic-angle spinning with variable-amplitude cross polarization, and TPPM decoupling at 63 kHz. The samples were spun at 12.0 kHz, and a total of 1024 scans were collected with a recycle delay of 5 seconds. A line broadening of 10 Hz was applied to the spectrum before FT was performed. Chemical shifts are reported using poly(tetrafluoroethylene) (Teflon®) as an external secondary reference which was assigned a chemical shift of −122 ppm.

Differential scanning calorimeter (DSC) data were acquired using TA Instruments DSC 2910 or equivalent instrumentation. Between 1 and 6 mg sample is weighed into an open pan. This pan is then crimped and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 200° C. The heating program is started. When the run is completed, the data are analyzed using the DSC analysis program contained in the system software. The melting endotherm is integrated between baseline temperature points that are above and below the temperature range over which the endotherm is observed. The data reported are the onset temperature, peak temperature and enthalpy.

Modulated differential scanning calorimeter (MDSC) data were acquired using TA Instruments DSC Q1000 or equivalent instrumentation. Between 1 and 10 mg sample was weighed into an open pan and lid was placed lightly to cover the sample. This covered pan was then placed at the sample position in the calorimeter cell. An empty pan with lid was placed at the reference position. The calorimeter cell was closed and a flow of nitrogen was passed through the cell. Method parameters for MDSC included heating to 80° C. at a rate of 10° C./min, isothermal at 80° C. for 10 mins, cooling to −40° C. at a rate of 10° C./min, and heating to 175° C. at a rate of 3° C./min with modulation of ±1° C./min. The heating program was started. When the run was completed, the data were analyzed using the DSC analysis program contained in the system software. The glass transition temperature ($T_g$) was integrated above and below the temperature range which baseline shifted is observed on reversible heat flow curve. In some amorphous sample, recrystallization is observed. The data reported are the onset temperature, midpoint temperature, and endset temperature of glass transition. The recrystallization exotherm is integrated between baseline temperature points that are above and below the temperature range over which the exotherm is observed. The data reported in this case are peak temperature and enthalpy.

FIG. 1 shows the X-ray powder diffraction pattern of the anhydrous crystalline tosylate salt of Compound I, Form A. Form A has characteristic diffraction peaks corresponding to d-spacings of 17.77, 8.90, 5.17, 4.45, 4.09, 3.32, 7.29, 4.20 and 3.81 angstroms. In particular, Form A can be characterized by having an XRPD pattern obtained using CuKα radiation containing at least one diffraction peak corresponding to a d-spacing selected from the group consisting of 17.77, 8.90, 5.17, 4.45, 4.09, 3.32, 7.29, 4.20 and 3.81 angstroms. More particularly, Form A can be characterized by having an XRPD pattern obtained using CuKα radiation containing at least two diffraction peaks corresponding to d-spacings selected from the group consisting of 17.77, 8.90, 5.17, 4.45, 4.09, 3.32, 7.29, 4.20 and 3.81 angstroms. Even more particularly, Form A can be characterized by having an XRPD pattern obtained using CuKα radiation containing at least three diffraction peaks corresponding to d-spacings selected from the group consisting of 17.77, 8.90, 5.17, 4.45, 4.09, 3.32, 7.29, 4.20 and 3.81 angstroms.

Form A can also be characterized by having at least one d-spacing selected from 17.77, 8.90 and 5.17 angstroms; or at least two d-spacings selected from 17.77, 8.90 and 5.17 angstroms.

Form A can also be characterized by having characteristic diffraction peaks corresponding to d-spacings of 17.77, 8.90, and 5.17 angstroms; or Form A can be characterized by having characteristic diffraction peaks corresponding to d-spacings of 4.45, 4.09 and 3.32 angstroms; or Form A can be characterized by diffraction peaks corresponding to d-spacings of 7.29, 4.20, and 3.81 angstroms. Furthermore, Form A can be characterized by a combination of two or three d-spacing groupings selected from (a) 17.77, 8.90, and 5.17 angstroms, (b) 4.45, 4.09 and 3.32 angstroms and (c) 7.29, 4.20, and 3.81 angstroms.

Anhydrous crystalline Form A can also be characterized by the X-ray diffraction pattern of FIG. 1.

Figure 2:
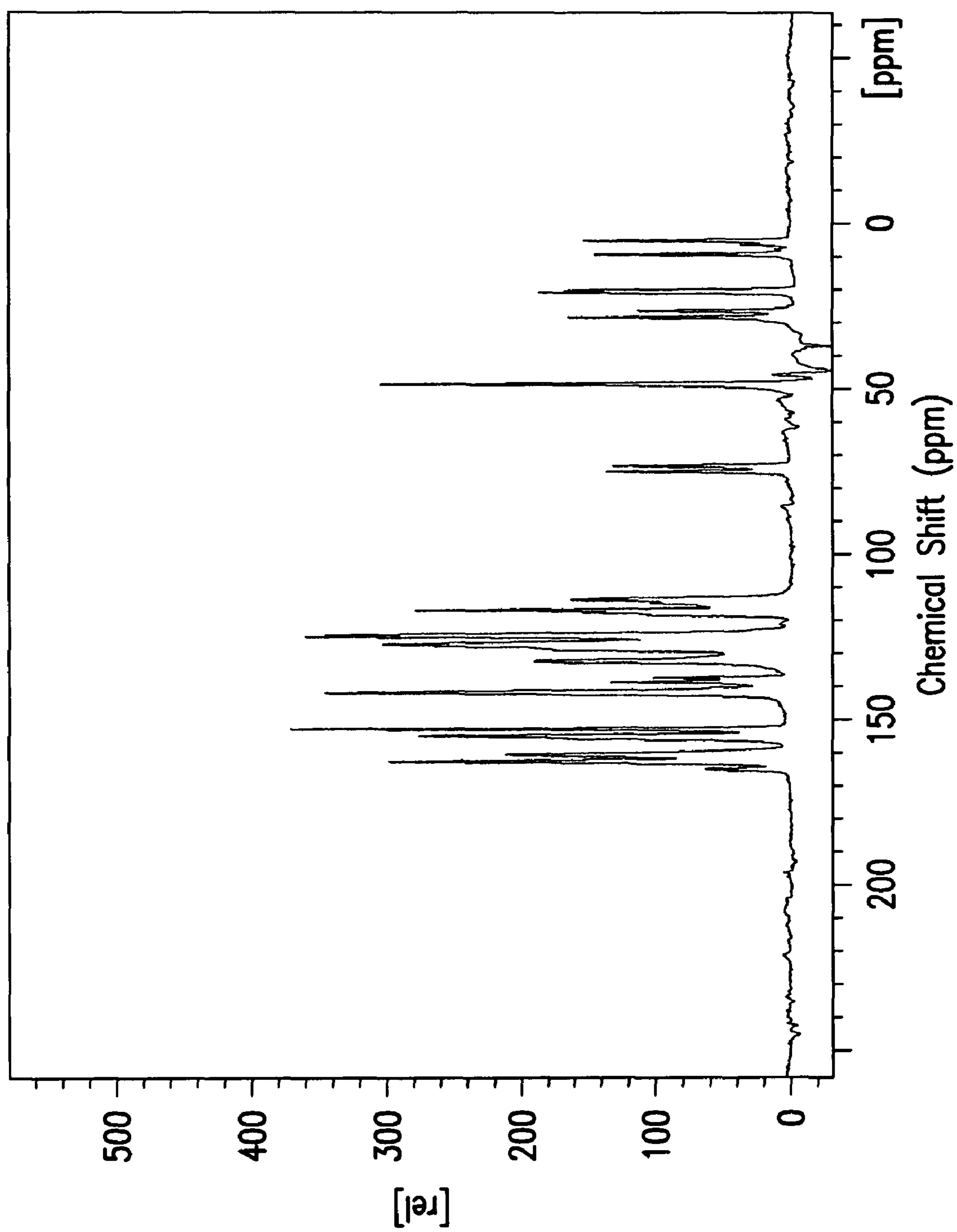
FIG. 2 is a solid-state carbon-13 cross-polarization magic-angle spinning (CPMAS) nuclear magnetic resonance (NMR) spectrum of the anhydrous crystalline Compound I tosylate salt, Form A.

FIG. 2 shows the solid-state carbon-13 CPMAS NMR spectrum for the anhydrous crystalline tosylate salt of Compound I, Form A. Form A exhibited characteristic signals with chemical shift values of 48.5, 124.1, 152.4, 28.4, 141.3, 162.1, 74.8, 154.4 and 164.5 parts per million (p.p.m. or ppm). In particular, Form A can be characterized by having at least one chemical shift value obtained by solid-state carbon-13 CPMAS NMR selected from the group consisting of 48.5, 124.1, 152.4, 28.4, 141.3, 162.1, 74.8, 154.4 and 164.5 p.p.m. More particularly, Form A can be characterized by having at least two chemical shift values obtained by solid-state carbon-13 CPMAS NMR selected from the group consisting of 48.5, 124.1, 152.4, 28.4, 141.3, 162.1, 74.8, 154.4 and 164.5 p.p.m. Even more particularly, Form A can be characterized by having at least three chemical shift values obtained by solid-state carbon-13 CPMAS NMR selected from the group consisting of 48.5, 124.1, 152.4, 28.4, 141.3, 162.1, 74.8, 154.4 and 164.5 p.p.m.

Form A can also be characterized by signals obtained by solid-state carbon-13 CPMAS NMR with chemical shift values of 48.5 and 124.1; or 48.5 and 152.4 p.p.m.

Form A can be characterized by signals obtained by solid-state carbon-13 CPMAS NMR with chemical shift values of 48.5, 124.1, and 152.4 p.p.m; or Form A can be characterized by signals with chemical shift values of 28.4, 141.3, and 162.1 p.p.m.; or Form A can be characterized by signals with chemical shift values of 74.8, 154.4, and 164.5 p.p.m. Furthermore, Form A can be characterized by a combination of two or three chemical shift values groupings selected from (a) 48.5, 124.1 and 152.4 p.p.m., (b) 28.4, 141.3 and 162.1 p.p.m. and (c) 74.8, 154.4 and 164.5 p.p.m.

Anhydrous crystalline Form A can also be characterized by the solid-state carbon-13 CPMAS NMR spectrum of FIG. 2.

Figure 3:
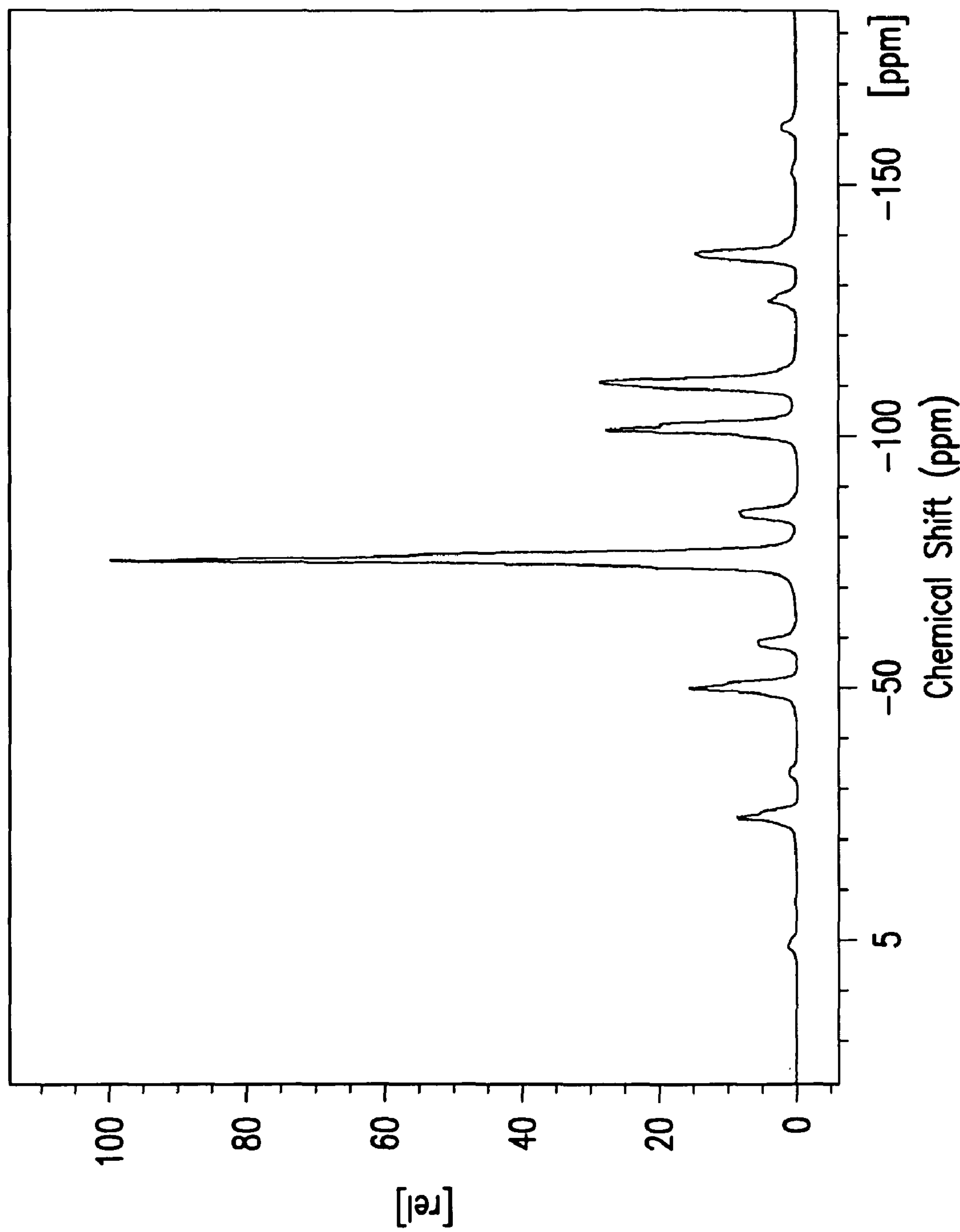
FIG. 3 is a solid-state fluorine-19 cross-polarization magic-angle spinning (CPMAS) nuclear magnetic resonance (NMR) spectrum of the anhydrous crystalline Compound I tosylate salt, Form A.

FIG. 3 shows the solid-state fluorine-19 CPMAS NMR spectrum for the anhydrous crystalline tosylate salt of Compound I, Form A. Form A exhibited characteristic signals with chemical shift values of −50.2, −75.6, −101.3, −24.6 and −110.9 p.p.m. In particular, Form A can be characterized by having at least one chemical shift value obtained by solid-state fluorine-19 CPMAS NMR selected from the group consisting of −50.2, −75.6, −101.3, −24.6 and −110.9 p.p.m. More particularly, Form A can be characterized by having at least two chemical shift values obtained by solid-state fluorine-19 CPMAS NMR selected from the group consisting of −50.2, −75.6, and −101.3, −24.6 and −110.9 p.p.m. Even more particularly, Form A can be characterized by having at least three chemical shift values obtained by solid-state fluorine-19 CPMAS NMR selected from the group consisting of −50.2, −75.6 and −101.3, −24.6 and −110.9 p.p.m.

Form A can also be characterized by having at least one chemical shift value obtained by solid-state fluorine-19 CPMAS NMR selected from the group consisting of −50.2, −75.6 and −101.3, or more particularly by having at least two chemical shift values selected from the group consisting of −50.2, −75.6 and −101.3.

Form A can also be characterized by signals obtained by solid-state fluorine-19 CPMAS NMR with chemical shift values of −50.2, −75.6, −101.3 p.p.m; or Form A can be characterized by signals with chemical shift values of −24.6 and −110.9 p.p.m. Anhydrous crystalline Form A can also be characterized by the solid-state fluorine-19 CPMAS NMR spectrum of FIG. 3.

Figure 4:
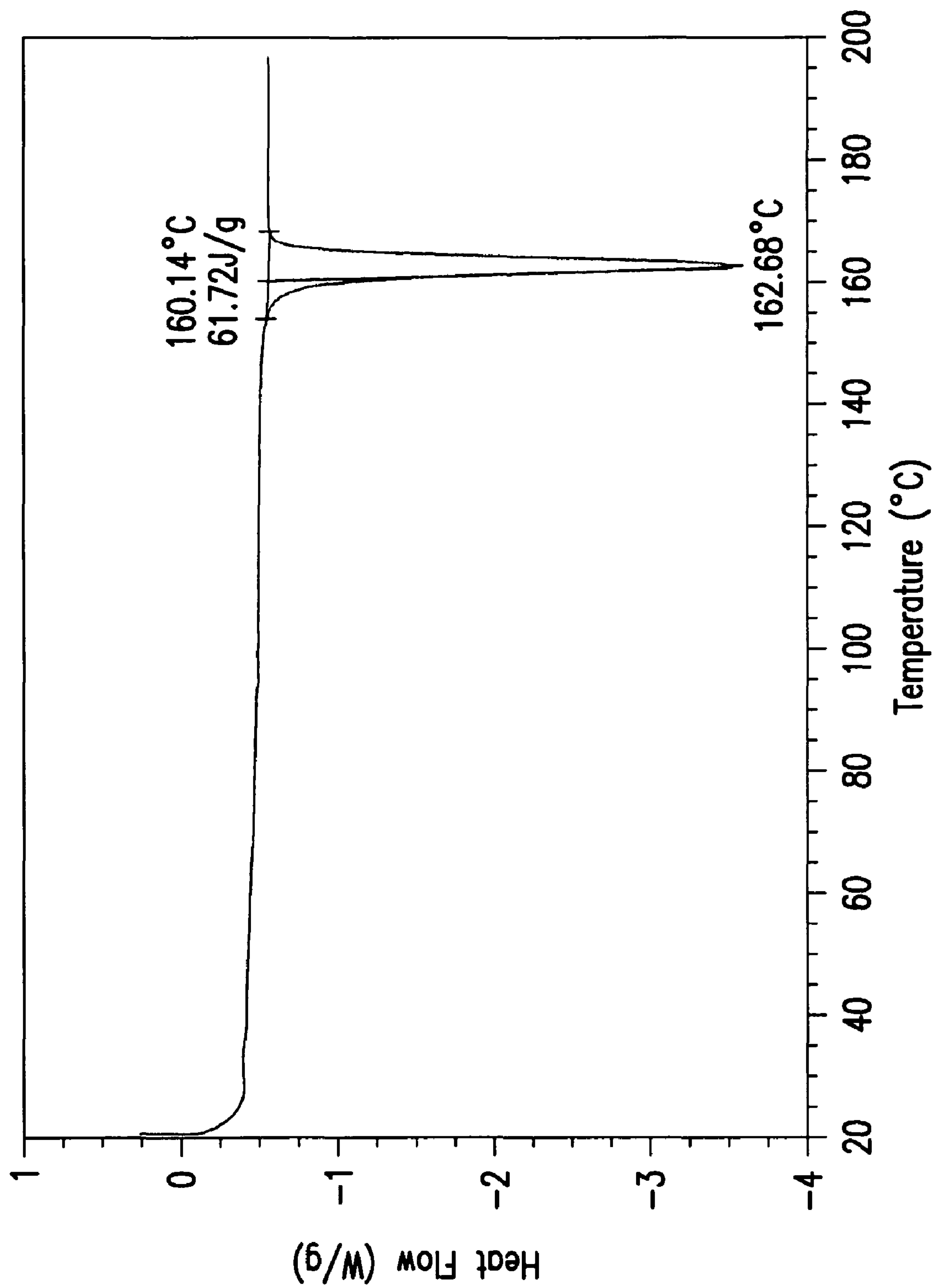
FIG. 4 is a typical differential scanning calorimeter (DSC) curve of the anhydrous crystalline Compound I tosylate salt, Form A.

FIG. 4 shows the differential calorimetry scan for the crystalline anhydrous tosylate salt Form A. Form A exhibited a single endotherm due to melting with an onset temperature of 160.1° C. Form A also exhibited a peak temperature of 162.7° C. Form A further exhibited and an enthalpy change of 61.7 J/g.

Figure 5:
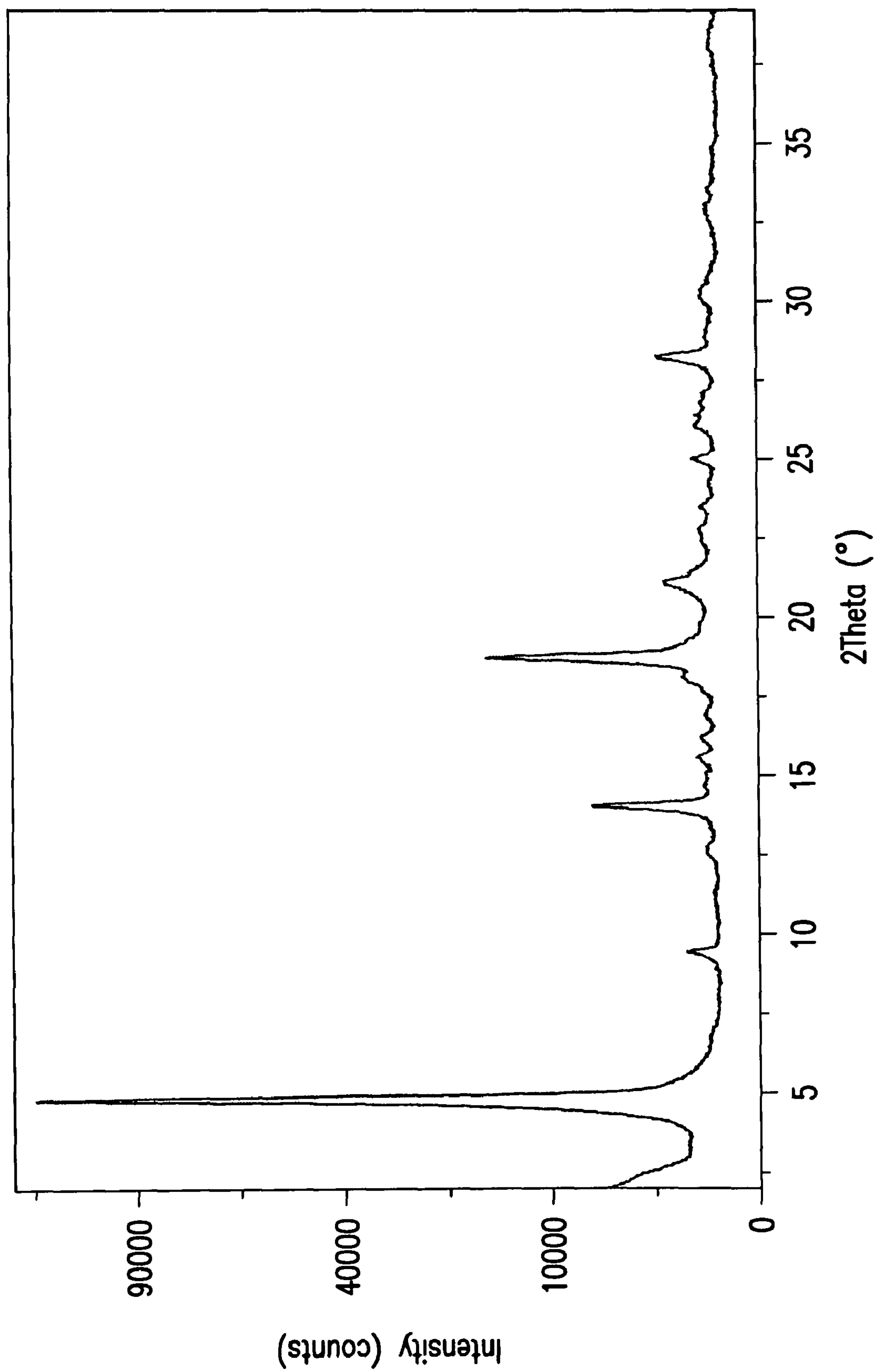
FIG. 5 is a characteristic X-ray diffraction pattern (XRPD) of the crystalline i-propylacetate (iPAc) solvate of Compound I tosylate salt, Form B.

The crystalline iPAc solvate of the tosylate salt of Compound I is referred to herein as Form B. FIG. 5 shows the X-ray powder diffraction pattern of the crystalline iPAc solvate tosylate salt Form B. Form B has characteristic diffraction peaks corresponding to d-spacings of 19.00, 6.36, 4.77, 5.74, 4.25, 3.19, 5.50, 5.27 and 3.60 angstroms. In particular, Form B can be characterized by having an XRPD pattern obtained using CuKα radiation containing at least one d-spacing selected from the group consisting of 19.00, 6.36, 4.77, 5.74, 4.25, 3.19, 5.50, 5.27 and 3.60 angstroms. More particularly, Form B can be characterized by having an XRPD pattern obtained using CuKα radiation containing at least two d-spacings selected from the group consisting of 19.00, 6.36, 4.77, 5.74, 4.25, 3.19, 5.50, 5.27 and 3.60 angstroms. Even more particularly, Form B can be characterized by having an XRPD pattern obtained using CuKα radiation containing at least three d-spacings selected from the group consisting of 19.00, 6.36, 4.77, 5.74, 4.25, 3.19, 5.50, 5.27 and 3.60 angstroms.

Form B can also be characterized by having at least one d-spacing selected from 19.00, 6.36, and 4.77 angstroms; or at least two d-spacings selected from 19.00, 6.36, and 4.77 angstroms.

Form B can also be characterized by having characteristic diffraction peaks corresponding to d-spacings of 19.00, 6.36, and 4.77 angstroms; or Form B can be characterized by having characteristic diffraction peaks corresponding to d-spacings of 5.74, 4.25, and 3.19 angstroms; or Form B can be characterized by diffraction peaks corresponding to d-spacings of 5.50, 5.27, and 3.60 angstroms. Furthermore, Form B can be characterized by a combination of two or three d-spacing groupings selected from (a) 19.00, 6.36, and 4.77 angstroms, (b) 5.74, 4.25, and 3.19 angstroms and (c) 5.50, 5.27, and 3.60 angstroms.

Form B can also be characterized by the X-ray diffraction pattern of FIG. 5.

Figure 6:
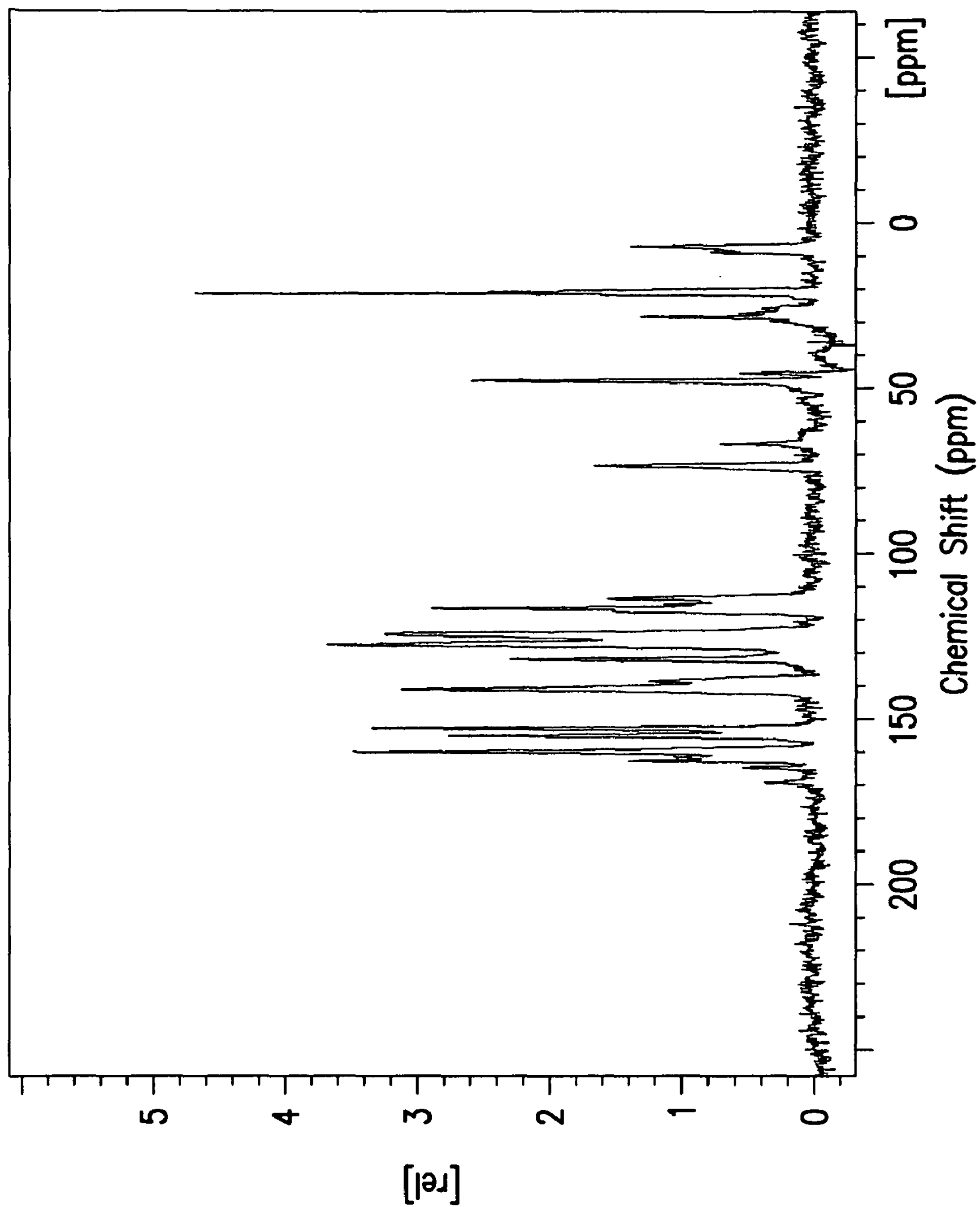
FIG. 6 is a solid-state carbon-13 cross-polarization magic-angle spinning (CPMAS) nuclear magnetic resonance (NMR) spectrum of the crystalline i-propylacetate (iPAc) solvate of Compound I tosylate salt, Form B.

FIG. 6 shows the solid-state carbon-13 CPMAS NMR spectrum for Form B. Form B exhibited characteristic signals with chemical shift values of 73.6, 127.5, 159.7, 124.2, 140.9, 152.5, 116.4, 131.9, and 154.9. In particular, Form B can be characterized by having at least one chemical shift value obtained by solid-state carbon-13 CPMAS NMR selected from the group consisting of 73.6, 127.5, 159.7, 124.2, 140.9, 152.5, 116.4, 131.9, and 154.9 p.p.m. More particularly, Form B can be characterized by having at least two chemical shift values obtained by solid-state carbon-13 CPMAS NMR selected from the group consisting of 73.6, 127.5, 159.7, 124.2, 140.9, 152.5, 116.4, 131.9, and 154.9 p.p.m. Even more particularly, Form B can be characterized by having at least three chemical shift values obtained by solid-state carbon-13 CPMAS NMR selected from the group consisting of 73.6, 127.5, 159.7, 124.2, 140.9, 152.5, 116.4, 131.9, and 154.9 p.p.m.

Form B can also be characterized by signals obtained by solid-state carbon-13 CPMAS NMR with at least one chemical shift value selected from 73.6, 127.5, and 159.7 p.p.m; or at least two chemical shift values selected from 73.6, 127.5, and 159.7 p.p.m Form B can also be characterized by signals obtained by solid-state carbon-13 CPMAS NMR with chemical shift values of 73.6, 127.5, and 159.7 p.p.m; or Form B can be characterized by signals with chemical shift values of 124.2, 140.9, and 152.5 p.p.m.; or Form B can be characterized by signals with chemical shift values of 116.4, 131.9, and 154.9 p.p.m. Furthermore, Form B can be characterized by a combination of two or three chemical shift values groupings selected from (a) 73.6, 127.5, and 159.7 p.p.m., (b) 124.2, 140.9, and 152.5 p.p.m. and (c) 116.4, 131.9, and 154.9 p.p.m.

Form B can also be characterized by the solid-state carbon-13 CPMAS NMR spectrum of FIG. 6.

Figure 7:
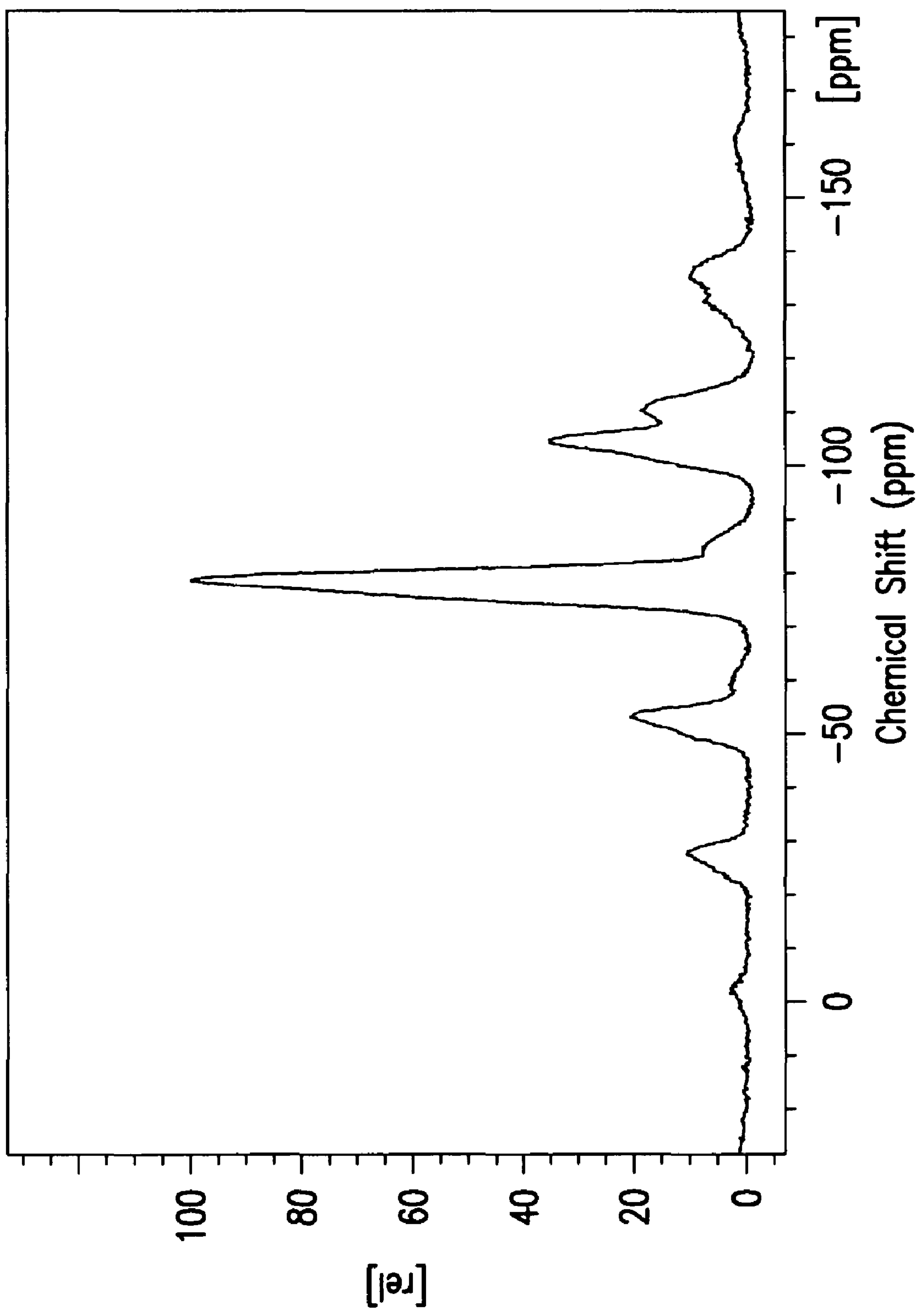
FIG. 7 is a solid-state fluorine-19 cross-polarization magic-angle spinning (CPMAS) nuclear magnetic resonance (NMR) spectrum of the amorphous form of Compound I tosylate salt.

FIG. 7 shows the solid-state fluorine-19 CPMAS NMR spectrum for the amorphous tosylate salt of Compound I. Compound I amorphous tosylate salt exhibited characteristic signals with chemical shift values of −53.2, −78.7, −104.7, −28.0 and −110.6 p.p.m. In particular, the amorphous tosylate salt can be characterized by having at least one chemical shift value obtained by solid-state fluorine-19 CPMAS NMR selected from the group consisting of −53.2, −78.7, −104.7, −28.0 and −110.6 p.p.m. More particularly, the amorphous tosylate salt can be characterized by having at least two chemical shift values obtained by solid-state fluorine-19 CPMAS NMR selected from the group consisting of −53.2, −78.7, −104.7, −28.0 and −110.6 p.p.m. Even more particularly, the amorphous tosylate salt can be characterized by having at least three chemical shift values obtained by solid-state fluorine-19 CPMAS NMR selected from the group consisting of −53.2, −78.7, −104.7, −28.0 and −110.6 p.p.m.

Additionally, the Compound I amorphous tosylate salt can be characterized by signals obtained by solid-state fluorine-19 CPMAS NMR with chemical shift values of −53.2, −78.7, and −104.7 p.p.m.; or the amorphous tosylate salt can be characterized by signals with chemical shift values of −28.0 and −110.6 p.p.m.

The amorphous tosylate salt of Compound I can also be characterized by the solid-state fluorine-19 CPMAS NMR spectrum of FIG. 7.

Figure 8:
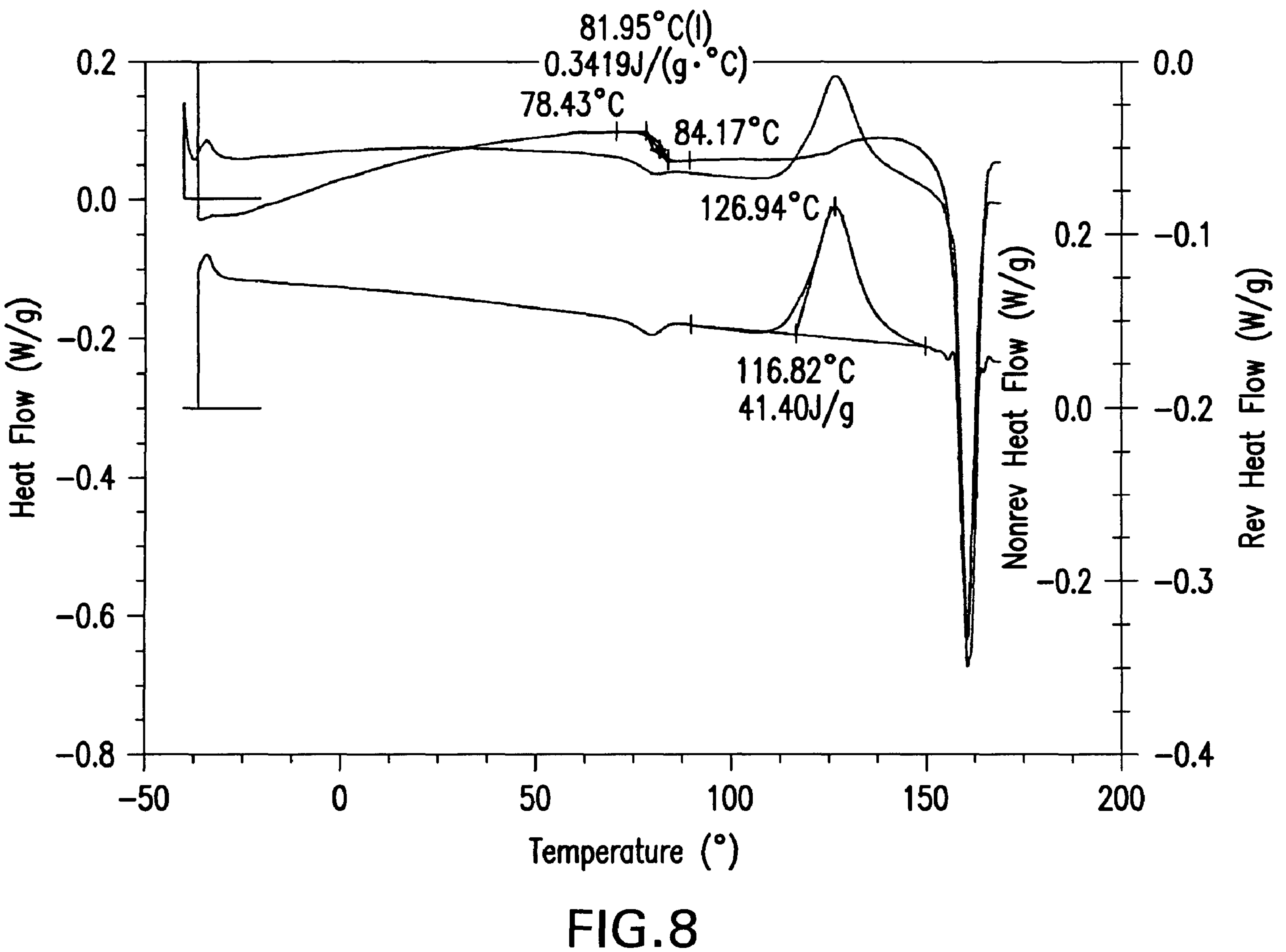
FIG. 8 is a typical modulated differential scanning calorimeter (MDSC) curve of the amorphous form of Compound I tosylate salt.

FIG. 8 shows the modulated differential calorimetry scan for the amorphous tosylate salt of Compound I. The heat capacity change observed in the reversible heat flow curve with a midpoint temperature of 81.95° C. corresponds to the glass transition of amorphous tosylate salt. A single exotherm due to recrystallization to crystalline tosylate salt Form A with an onset temperature of 116.8° C., a peak temperature of 126.9° C., and an enthalpy change of 41.4 J/g is also observed. The crystalline tosylate salt then melts at approximately 160° C. The recrystallization exotherms may not always be observed in some amorphous tosylate salt.

Compound I is a pharmacologically active agent having 5-LO inhibitory activity, and accordingly the salts of Compound I likewise are active 5-LO inhibitors. The ability of Compound I and salts thereof to inhibit biosynthesis of the leukotrienes makes them useful for preventing or reversing the symptoms induced by leukotrienes in a human subject. Accordingly, this invention provides a method for preventing the synthesis, the action, or the release of leukotrienes in a mammal which comprises administering to said mammal a 5-LO inhibitory effective amount of a salt of Compound I in a pharmaceutical composition of this invention. Such 5-LO inhibitory activity can be measured using the Human 5-Lipoxygenase Enzyme Assay and 5-Lipoxygenase Human Whole Blood Assay described herein. Since leukotrienes are potent inflammatory mediators, also provided is a method of treating an inflammatory condition in a mammal which comprises administering a therapeutically effective amount of a compound of this invention to a mammal in need of such treatment.

The inhibition of the mammalian biosynthesis of leukotrienes also indicates that the salts of Compound I and pharmaceutical compositions thereof are useful to treat, prevent or ameliorate atherosclerosis in mammals, and especially in humans. Therefore, the compounds of this invention can be used for the treatment of atherosclerosis comprising administering a therapeutically effective amount of a compound of this invention to a patient in need of such treatment.

The method of this invention serves to prevent or slow new atherosclerotic lesion or plaque formation, and to prevent or slow progression of existing lesions or plaques, as well as to cause regression of existing lesions or plaques. Accordingly, one aspect of this invention encompassed within the scope of treatment of atherosclerosis involves a method for halting or slowing the progression of atherosclerosis, including halting or slowing atherosclerotic plaque progression, comprising administering a therapeutically effective amount of a compound of this invention to a patient in need of such treatment. This method includes halting or slowing progression of atherosclerotic plaques existing at the time the instant treatment is begun (i.e., "existing atherosclerotic plaques"), as well as halting or slowing formation of new atherosclerotic plaques in patients with atherosclerosis.

Another aspect of this invention encompassed within the scope of treatment of atherosclerosis involves a method for effecting regression of atherosclerosis, including effecting regression of atherosclerotic plaques existing at the time the instant treatment is begun, comprising administering a therapeutically effective amount of a compound of this invention to a patient in need of such treatment.

Also provided is a method comprising administering to a patient who has atherosclerosis a compound of this invention with the objective of preventing or reducing the risk of atherosclerotic plaque rupture. Therefore, this invention provides a method for preventing or reducing the risk of atherosclerotic plaque rupture comprising administering a prophylactically effective amount of a compound of this invention to a patient having atherosclerotic plaque.

This invention also involves a method for preventing or reducing the risk of developing atherosclerosis, comprising administering a prophylactically effective amount of a compound of this invention to a patient in need of such treatment, including for example, a patient who is at risk for developing atherosclerosis.

Atherosclerosis is characterized by the deposition of atheromatous plaques containing cholesterol and lipids on the innermost layer of the walls of large and medium-sized arteries. Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction, are all clinical manifestations of atherosclerosis and are therefore encompassed by the terms "atherosclerosis" and "atherosclerotic disease."

A compound of the instant invention may be administered to prevent or reduce the risk of occurrence, or recurrence where the potential exists, of a coronary heart disease (CHD) event, a cerebrovascular event, and/or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Accordingly, the instant invention also provides a method for preventing or reducing the risk of a first or subsequent occurrence of an atherosclerotic disease event comprising the administration of a prophylactically effective amount of a compound of this invention to a patient in need of such treatment, such as a patient who is at risk for such an event. The patient in need of such treatment may already have atherosclerotic disease at the time of administration, or may be at risk for developing it.

This invention also provides a method for treating, preventing, or ameliorating angina and/or myocardial ischemia, comprising administering a therapeutically or prophylactically effective amount, as appropriate, of a compound of this invention to a patient in need of such treatment.

Additionally, the activity of the instant compounds as leukotriene biosynthesis inhibitors makes them useful for treating, preventing, or ameliorating: 1) pulmonary disorders including diseases such as asthma, chronic bronchitis, and related obstructive airway diseases, 2) allergies and allergic reactions such as allergic rhinitis, contact dermatitis, allergic conjunctivitis, and the like, 3) inflammation such as arthritis or inflammatory bowel disease, 4) pain, 5) skin disorders such as atopic eczema, and the like, 6) cardiovascular disorders such hypertension, platelet aggregation and the like, 7) renal insufficiency arising from ischaemia induced by immunological or chemical (cyclosporin) etiology and 8) migraine or cluster headache, 9) ocular conditions such as uveitis, 10) hepatitis resulting from chemical, immunological or infectious stimuli, 11) trauma or shock states such as burn injuries, endotoxemia and the like, 12) allograft rejection, 13) prevention of side effects associated with therapeutic administration of cytokines such as Interleukin II and tumor necrosis factor, 14) chronic lung diseases such as cystic fibrosis, bronchitis and other small- and large-airway diseases, 15) cholecystitis, 16) multiple sclerosis, 17) proliferation of myoblastic leukemia cells, 18) pulmonary fibrosis, 19) respiratory syncytial virus, 20) acne and 21) sleep apnea. Moreover, the compounds of this invention can be administered to patients, including adult and pediatric patients, for the relief of symptoms of allergic rhinitis, including seasonal allergic rhinitis.

Particularly, the compounds of this invention can be administered to patients, including adult and pediatric patients, for the prophylaxis of asthma and for chronic treatment of asthma. The compounds of this invention can be administered to patients, including adult and pediatric patients, for the treatment of asthma: (1) as an alternative to low-dose inhaled corticosteroids (ICS) for patients with mild persistent asthma, (2) as concomitant therapy with low-dose inhaled corticosteroids (ICS) for patients with mild persistent asthma, or (3) as concomitant therapy in patients with persistent asthma who are inadequately controlled on inhaled corticosteroids (ICS) or on combined ICS/long-acting beta-agonist (LABA) therapy. The compounds can be used for treatment of asthmatic patients including, but not limited to, steroid resistant/non-responder asthmatics, asthmatics for whom leukotriene modifiers have previously failed, smoking asthmatics, and aspirin sensitive asthmatics.

The compounds can be administered to patients to: (1) improve FEVI (Forced Expitory Volume in one minute), (2) improve morning and evening PEF (Peak Expitory flow), (3) reduce beta-agonist use (measured by puffs/day), (4) reduce inhaled/systemic steroid use, (5) improve daytime asthma symptoms, (6) reduce number of nocturnal awakenings, (7) improve asthma control days, (8) reduce number of asthma exacerbations, wherein an exacerbation is defined as: requiring systemic steroid, an emergency room visit, hospitalization, an unscheduled asthma related doctor visit, decrease in A.M. PEF by >20% or A.M. PEF <180 l/min, increased SABA (short-acting beta-agonist) use >70% from baseline (minimum increase 2 puffs), or increased symptom score of >50%, (9) reduce the number of asthma attacks (measured as % of days with at least one attack over a specified period of total days), wherein the attack is one that requires systemic steroid use, an emergency room visit, hospitalization, or an unscheduled asthma related doctor visit, (10) reduce the number of acute asthma attacks, (11) reduce blood and sputum eosinophils, and/or (12) prevent and treat EIB (exercised induced bronchoconstriction).

The compounds of the present invention may also be used to treat or prevent mammalian (especially, human) disease states such as erosive gastritis; erosive esophagitis; diarrhea; cerebral spasm; premature labor; spontaneous abortion; dysmenorrhea; ischemia; noxious agent-induced damage or necrosis of hepatic, pancreatic, renal, or myocardial tissue; liver parenchymal damage caused by hepatoxic agents such as $CCl_4$ and D-galactosamine; ischemic renal failure; disease-induced hepatic damage; bile salt induced pancreatic or gastric damage; trauma- or stress-induced cell damage; and glycerol-induced renal failure. Leukotriene biosynthesis inhibitors also act as inhibitors of tumor metastasis and exhibit cytoprotective action.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions, and the like. Two assays can be used to measure cytoprotective ability. These assays are: (A) an ethanol-induced lesion assay and (B) an indomethacin-induced ulcer assay and are described in EP 140,684. In particular, the compounds of the invention would be useful to reduce the gastric erosion caused by co-administration of a cyclooxygenase-2 selective inhibitor such as etoricoxib (ARCOXIA™), and celecoxib (CELEBREX®) and low-dose aspirin.

In addition, the compounds of this invention can also be used for the treatment of chronic obstructive pulmonary disease (COPD). As described in S. Kilfeather, Chest, 2002, vol. 121, 197, airway neutrophilia in COPD patients is believed to be a contributing source of inflammation and is associated with airway remodeling. The presence of neutrophils is mediated in part by $LTB_4$, and treatment with the instant compounds could be used to reduce neutrophilic inflammation in patients with COPD and reduce the rate of COPD exacerbations. In particular, the compounds of this invention could be used for daily, preferably once-daily, maintenance treatment of airflow obstruction associated with COPD, including chronic bronchitis and emphysema.

Additionally, the 5-LO inhibitor compounds of this invention may be useful for treatment of psychiatric disorders, such as depression and anxiety; see Manev, R. and Manev, H., "5-Lipoxygenase as a Putative Link Between Cardiovascular and Psychiatric Disorders," *Critical Reviews in Neurobiology,* 16: 181-186 (2004). The 5-LO inhibitor compounds inhibitors of this invention can also be used in a therapeutically effective amount for promoting osteogenesis in a patient in need of such treatment. For example, the compounds could be used to promote osteogenesis to accelerate or enhance bone fracture healing, treat bone defects, and enhance bone formation. The compounds can be administered alone or in combination with one or more additional active agents that inhibit bone resorption, regulate calcium resorption from bone, enhance bone accumulation, enhance bone formation, induce bone formation, impair growth of microorganisms, reduce inflammation, and/or reduce pain.

The term "patient" includes mammals, especially humans, who use the instant active agents for the prevention or treatment of a medical condition. Administering of the drug to the patient includes both self-administration and administration to the patient by another person. The patient may be in need of treatment for an existing disease or medical condition, or may desire prophylactic treatment to prevent or reduce the risk for diseases and medical conditions affected by inhibition of leukotriene biosynthesis.

The term "therapeutically effective amount" is intended to mean that amount of a drug or pharmaceutical agent that will elicit the biological or medical response of a tissue, a system, animal or human that is being sought by a researcher, veterinarian, medical doctor or other clinician. The term "prophylactically effective amount" is intended to mean that amount of a pharmaceutical drug that will prevent or reduce the risk of occurrence of the biological or medical event that is sought to be prevented in a tissue, a system, animal or human by a researcher, veterinarian, medical doctor or other clinician.

Dosage amounts described herein are based on the weight of the pharmaceutically active free-base Compound I. The magnitude of prophylactic or therapeutic dose of a compound of this invention will, of course, vary with the nature of the severity of the condition to be treated and its route of administration. It will also vary according to the age, weight and response of the individual patient. It is understood that a specific daily dosage amount can simultaneously be both a therapeutically effective amount, e.g., for treatment to slow progression of existing atherosclerosis, and a prophylactically effective amount, e.g., for prevention of an atherosclerotic disease event or formation of new lesions. In general, the daily dose range for anti-asthmatic, anti-inflammatory (including COPD treatment), anti-allergic (including allergic rhinitis) or anti-atherosclerotic use and generally, uses other than cytoprotection, can lie within the range of from about 0.01 mg to about 3 mg per kg body weight of a mammal, particularly a human, preferably 0.1 mg to about 2.5 mg per kg, in single or divided doses, and preferably in a single daily dose. On the other hand, it may be necessary to use dosages outside these limits in some cases.

In the case where an oral composition is employed, a suitable daily dosage range for human anti-asthmatic, anti-inflammatory, anti-allergic or anti-atherosclerotic use is, e.g., from about 1 mg to about 200 mg, and more particularly from about 10 mg to about 150 mg, preferably in a single daily dose. For example, for anti-asthmatic use a daily dosage amount can range from about 10 mg to about 100 mg, for example 10 mg, 50 mg or 100 mg may be employed. For COPD treatment a daily dosage amount could be for example 100 mg, and for atherosclerosis treatment a daily dosage amount could be for example 150 mg. However, suitable daily dosage amounts are not limited to these examples. Tablets and capsules such as dry filled capsules are preferred oral formulations for use in adult patients. Chewable or oral disintegrating formulations may also be used, particularly for formulation intended for the pediatric population.

For inhaled formulations, the dosage amount per administration is generally lower than that for an oral formulation such as a tablet or capsule. For example, a daily dose of the active compound administered via an inhaled formulation may range from 0.010 mg to 10 mg, and particularly from 0.010 mg to 2.5 mg. Single or multiple inhaled doses may be used per day, but a single inhaled dose is preferred.

The active compound may be used for the prevention and/or treatment in children of asthma as well as allergic rhinitis. For pediatric use, the daily dosage range is expected to be lower than that for adult use. For example, a suitable pediatric daily dosage amount may range from 1 mg to 200 mg per day, and particularly from 1 mg to 50 mg per day. Dosage amounts contained in oral formulations and inhaled formulations for pediatric use would need to be adjusted accordingly. A single daily dose is preferred, although divided doses can be used. Preferred pediatric oral formulations include an oral granule formulation (e.g. a sprinkle), chewable tablets and oral disintegrating solid formulations such as a disintegrating tablet. Drinkable syrups may also be employed. Taste masking technology may be employed with these or any other formulations described herein as needed.

For use where a composition for intravenous administration is employed, a suitable daily dosage range for anti-asthmatic, anti-inflammatory, anti-atherosclerotic or anti-allergic use is from about 0.001 mg to about 25 mg (preferably from 0.01 mg to about 1 mg) of a compound of this invention per kg of body weight per day and for cytoprotective use from about 0.1 mg to about 100 mg (preferably from about 1 mg to about 100 mg and more preferably from about 1 mg to about 10 mg) of a compound of this invention per kg of body weight per day. For the treatment of diseases of the eye, ophthalmic preparations for ocular administration comprising 0.001-1% by weight solutions or suspensions of the compounds of this invention in an acceptable ophthalmic formulation may be used.

For cytoprotective use a suitable daily dosage range is from 0.1 mg to about 100 mg, preferably from about 1 mg to about 100 mg, and more preferably from about 10 mg to about 100 mg, of a compound of this invention per kg of body weight per day. The exact amount of a compound of this invention to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of this invention in avoiding future damage would be co-administration of a compound of this invention with an NSAID that might otherwise cause such damage (for example, indomethacin). For such use, the compound of this invention is administered from 30 minutes prior up to 30 minutes after administration of the NSAID. Preferably it is administered prior to or simultaneously with the NSAID, (for example, in a combination dosage form). An oral formulation is preferred.

The pharmaceutical compositions of the present invention comprise a salt of Compound I of this invention and a pharmaceutically acceptable carrier and optionally other therapeutic ingredients. The salt of Compound I in the pharmaceutical compositions may be in the amorphous form or may be a crystalline form, such as a crystalline form characterized hereinabove. Any suitable route of administration may be employed for providing a mammal, especially a human with an effective dosage of a compound of the present invention. For example, oral, rectal, topical, parenteral (including subcutaneous, intramuscular, and intravenous), ocular (ophthalmic), pulmonary (nasal or buccal inhalation), and the like may be employed, although the most suitable route in any given case will depend on the nature and severity of the condition being treated. They may be conveniently presented in unit dosage form and prepared by any of the methods well-known in the art of pharmacy. Dosage forms include for example tablets, troches, dispersions, suspensions, solutions, capsules including dry filled capsules, creams, ointments, aerosols, and the like. Oral formulations are preferred for uses related to asthma, COPD, allergic rhinitis, atherosclerosis and prevention of atherosclerotic disease events. Additionally, inhaled formulations are desirable for treatment of asthma, COPD and allergic rhinitis. Other formulations may be used consistent with the nature of the condition being treated.

Pharmaceutical compositions of the present invention suitable for oral administration may be presented as discrete units such as capsules, cachets or tablets, each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each solid dosage form, e.g. tablet, or capsule, contains from about 1 mg to about 200 mg of the active ingredient on a free-base weight basis, for example but not limited to 1 mg, 5 mg, 10 mg, 20 mg, 25 mg, 30 mg, 40 mg, 50 mg, 60 mg, 70 mg, 75 mg, 80 mg, 90 mg, 100 mg, 125 mg, 150 mg, 175 mg and 200 mg.

For administration by inhalation, the salts of Compound I of the present invention are conveniently delivered in the form of an aerosol suitable for pulmonary drug delivery. These aerosol dosage forms include but are not limited to nebulized solutions and suspensions, metered-dose inhalers or dry powder inhalers. For nebulization the active ingredient(s) are typically formulated in an aqueous vehicle and administered by jet or electronic devices capable of generating a fine aerosol cloud. Metered-dose inhalers (MDI) use propellants such as hydrofluorocarbons to solubilize or suspend the active ingredient in a pressurized container capable of generating the disperse aerosol. For dry powder inhalation, the salts of Compound I are used alone or with excipients in conjunction with a delivery device capable for delivery of the active substance to the lung.

Suitable topical formulations of a compound of this invention include transdermal devices, aerosols, creams, ointments, lotions, dusting powders, and the like.

In practical use, the salts of Compound I of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the salts of Compound I of this invention may also be administered by controlled release means and/or delivery devices such as those described in U.S. Pat. Nos. 3,845,770; 3,916,899; 3,536,809; 3,598,123; 3,630,200; 4,008,719; and 5,366,738 the disclosures of which are incorporated herein by reference.

The following are examples of representative pharmaceutical dosage forms for the salts of Compound I of this invention (referred to as Active Compound):

| Injectable Suspension (I.M.) | mg/ml |
|---|---|
| Active Compound | 10 |
| Methylcellulose | 5.0 |
| Tween 80 | 0.5 |
| Benzyl alcohol | 9.0 |

-continued

| | |
|---|---|
| Benzalkonium chloride | 1.0 |
| Water for injection to a total volume of 1 ml | |

| Tablet | mg/tablet |
|---|---|
| Active Compound | 25 |
| Microcrystalline Cellulose | 415 |
| Povidone | 14.0 |
| Pregelatinized Starch | 43.5 |
| Magnesium Stearate | 2.5 |
| | 500 |
| Active Compound | 137 |
| Microcrystalline Cellulose | 167.75 |
| Lactose powder | 167.75 |
| Croscarmellose sodium | 15 |
| Colloidal Silica | 2.5 |
| Magnesium Stearate | 10 |
| | 500 |

| Capsule | mg/capsule |
|---|---|
| Active Compound | 25 |
| Lactose Powder | 573.5 |
| Magnesium Stearate | 1.5 |
| | 600 |
| Active Compound | 137 |
| Microcrystalline cellulose | 180.15 |
| Lactose Powder | 180.15 |
| Magnesium Stearate | 2.5 |
| | 500 |

The instant invention also encompasses a process for preparing a pharmaceutical composition comprising combining a compound of this invention with a pharmaceutically acceptable carrier. Also encompassed is the pharmaceutical composition which is made by combining a compound of this invention with a pharmaceutically acceptable carrier.

A therapeutically effective amount of a compound of this invention can be used for the preparation of a medicament useful for treating or preventing any of the medical conditions described herein, in dosage amounts described herein. For example, a compound of this invention can be used for the preparation of a medicament useful for preventing or reducing the risk of developing atherosclerotic disease, halting or slowing the progression of atherosclerotic disease once it has become clinically manifest, and preventing or reducing the risk of a first or subsequent occurrence of an atherosclerotic disease event. Additionally, a compound of this invention can be used for the preparation of a medicament useful for the treatment of asthma, allergies and allergic conditions, inflammation, COPD or erosive gastritis. The medicament comprised of a compound of this invention may also be prepared with one or more additional active agents, such as those described below.

One or more additional active agents may be used in combination with the compounds of this invention in a single dosage formulation, or the active agents of the combination may be administered to the patient in separate dosage formulations, which allows for concurrent or sequential administration of the active agents. Unless otherwise specified, reference herein to compounds of this invention being used in combination with other active agents or used as part of combination therapy or the like encompasses both a single pharmaceutical composition comprised of a compound of this invention with one or more additional active agents, as well as a pharmaceutical composition comprised of a compound of this invention administered as part of a combination therapy with one or more other separately formulated active agents.

In addition to the compounds of this invention, the pharmaceutical compositions of the present invention can also contain other active agents (i.e., ingredients) and the pharmaceutical compositions comprised of a compound of this invention may be used for combination therapy with one or more other separately formulated active agents, such as cyclooxygenase inhibitors, non-steroidal anti-inflammatory drugs (NSAIDs), peripheral analgesic agents such as zomepirac diflunisal and the like. The weight ratio of the compound of this invention to the second active ingredient may be varied and will depend upon the effective dose of each ingredient. Generally, an effective dose of each will be used. Thus, for example, when a compound of this invention is combined with an NSAID the weight ratio of the compound of said compound to the NSAID will generally range from about 1000:1 to about 1:1000, preferably about 200:1 to about 1:200. Combinations of a compound of this invention and other active ingredients will generally also be within the aforementioned range, but in each case, an effective dose of each active ingredient should be used.

NSAIDs can be characterized into five groups: (1) propionic acid derivatives, for example alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen; (2) acetic acid derivatives for example indomethacin, which is a preferred NSAID, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac; (3) fenamic acid derivatives such as flufenamic acid, meclofenamic acid, mefenamic acid, niflumic acid and tolfenamic acid; (4)oxicams, for example isoxicam, piroxicam, sudoxicam and tenoxican; and (5) biphenylcarboxylic acid derivatives for example diflunisal and flufenisal; or a pharmaceutically acceptable salt thereof.

In addition to indomethacin, other preferred NSAIDs are acetyl salicylic acid, diclofenac, fenbufen, fenoprofen, flurbiprofen, ibuprofen, ketoprofen, naproxen, phenylbutazone, piroxicam, sulindac, and tolmetin. Pharmaceutical compositions and combinations comprising compounds of this invention may also contain inhibitors of the biosynthesis of the leukotrienes such as are disclosed in EP 138,481 (Apr. 24, 1985), EP 115,394 (Aug. 8, 1984), EP 136,893 (Apr. 10, 1985), and EP 140,709 (May 8, 1985), which are hereby incorporated herein by reference.

The compounds of this invention may also be used in combination with leukotriene antagonists such as those disclosed in EP 106,565 (Apr. 25, 1984) and EP 104,885 (Apr. 4, 1984) which are hereby incorporated herein by reference and others known in the art such as those disclosed in EP Application Nos. 56,172 (Jul. 21, 1982) and 61,800 (Jun. 10, 1982); and in U.K. Patent Specification No. 2,058,785 (Apr. 15, 1981), which are hereby incorporated herein by reference.

Pharmaceutical compositions and combinations comprising compounds of this invention may also contain as the second active ingredient, or be used in combination therapy with, prostaglandin antagonists such as those disclosed in EP 11,067 (May 28, 1980) or thromboxane antagonists such as those disclosed in U.S. Pat. No. 4,237,160. They may also contain or be used with histidine decarboxylase inhibitors such as α-fluoromethylhistidine, described in U.S. Pat. No. 4,325,961. The compounds of this invention may also be advantageously combined with an $H_1$ or $H_2$-receptor antagonist, such as for instance acetamazole, aminothiadiazoles disclosed in EP 40,696 (Dec. 2, 1981), benadryl, cimetidine, famotidine, framamine, histadyl, phenergan, ranitidine, terfenadine and like compounds, such as those disclosed in U.S. Pat. Nos. 4,283,408; 4,362,736; and 4,394,508. The pharmaceutical compositions may also contain or be used in combination with a $K^+/H^+$ ATPase inhibitor such as omeprazole, disclosed in U.S. Pat. No. 4,255,431, and the like. Compounds of this invention may also be usefully combined with most cell stabilizing agents, such as 1,3-bis(2-carboxychromon-5-yloxy)-2-hydroxypropane and related compounds described in British Patent Specifications 1,144,905 and 1,144,906. Another useful pharmaceutical composition comprises compounds of this invention in combination with serotonin antagonists such as methysergide, the serotonin antagonists described in *Nature,* 316, 126-131 (1985), and the like. Each of the references referred to in this paragraph is hereby incorporated herein by reference.

Other advantageous pharmaceutical combinations comprise the compounds of this invention in combination with anti-cholinergics such as ipratropium bromide and tiotropium, bronchodilators such as the beta agonist salbutamol, metaproterenol, terbutaline, fenoterol, salmeterol, formoterol and the like, and the anti-asthmatic drugs theophylline, choline theophyllinate and enprofylline, the calcium antagonists nifedipine, diltiazem, nitrendipine, verapamil, nimodipine, felodipine, etc., and the corticosteroids, hydrocortisone, methylprednisolone, betamethasone, dexamethasone, beclomethasone, and the like.

Particularly, for the prophylaxis and treatment of asthma, compounds of this invention can be used in combination with orally inhaled corticosteroids, such as beclomethasone (e.g. QVAR® Inhalation Aerosol), budesonide (e.g. Pulmicort Respules), flunisolide (e.g., AEROBID® and AEROBID®-M Inhaler System), fluticasone (e.g., FLOVENT® DISKUS® inhalation powder, FLOVENT® HFA Inhalation Aerosol), mometasone (e.g., ASMANEX® TWISTHALER®), and triamcinolone (e.g., AZMACORT® Inhalation Aerosol), and also with inhaled corticosteroid/LABA products such as fluticasone propionate/salmeterol (e.g., ADVAIR DISKUS®). The instant compounds could also be used in combination with leukotriene receptor antagonists such as montelukast (e.g., SINGULAIR®); phosphodiesterase 4 (PDE4) inhibitors such as roflumilast, N-Cyclopropyl-1-[3-(1-oxido-3-pyridinylethynyl)phenyl]-1,4-dihydro[1,8]naphthyridin-4-one-3-carboxamide and the compounds disclosed in PCT Publication WO2003/018579; and Very Late Antigen 4 (VLA4) inhibitors such as the compounds disclosed in U.S. Pat. No. 6,229,011, particularly R411 (N-(2-Chloro-6-methylbenzoyl)-4-[(2,6-dichlorobenzoyl)amino]-L-phenylalanine-2-(diethylamino)ethyl ester which is an ester pro-drug of the active moiety, N-(2-chloro-6-methylbenzoyl)-4-[(2,6-dichlorobenzoyl)amino]-L-phenylalanine), and the compounds disclosed in PCT publication WO2006/023396.

Furthermore, additional active agents such as anti-atherosclerotic agents, anti-diabetes agents, anti-obesity agents and agents used for the treatment of metabolic syndrome, may be used in combination with the compounds of this invention. The additional active agent or agents can be lipid altering compounds such as HMG-CoA reductase inhibitors, or agents having other pharmaceutical activities, or agents that have both lipid-altering effects and other pharmaceutical activities. Examples of HMG-CoA reductase inhibitors useful for this purpose include statins in their lactonized or dihydroxy open acid forms and pharmaceutically acceptable salts and esters thereof, including but not limited to lovastatin (MEVACOR®; see U.S. Pat. No. 4,342,767); simvastatin (ZOCOR®; see U.S. Pat. No. 4,444,784); dihydroxy open-acid simvastatin, particularly the ammonium or calcium salts thereof; pravastatin, particularly the sodium salt thereof (PRAVACHOL®; see U.S. Pat. No. 4,346,227); fluvastatin particularly the sodium salt thereof (LESCOL®; see U.S. Pat. No. 5,354,772); atorvastatin, particularly the calcium salt thereof (LIPITOR®; see U.S. Pat. No. 5,273,995); pitavastatin also referred to as NK-104 (see PCT international publication number WO 97/23200); and rosuvastatin (CRESTOR®; see U.S. Pat. No. 5,260,440). Additional active agents which may be employed in combination with a compound of this invention include but are not limited to HMG-CoA synthase inhibitors; cholesterol absorption inhibitors such as ezetimibe (ZETIA®) which is 1-(4-fluorophenyl)-3(R)-[3(S)-(4-fluorophenyl)-3-hydroxypropyl)]-4(S)-(4-hydroxyphenyl)-2-azetidinone, described in U.S. Pat. Nos. Re. 37721 and 5,846,966 as well as a fixed dose combination of ezetimibe and simvastatin (VYTORIN®); HDL-raising agents such as cholesterol ester transfer protein (CETP) inhibitors, for example JTT-705 (Japan Tobacco Company); squalene epoxidase inhibitors; squalene synthetase inhibitors (also known as squalene synthase inhibitors); acyl-coenzyme A: cholesterol acyltransferase (ACAT) inhibitors including selective inhibitors of ACAT-1 or ACAT-2 as well as dual inhibitors of ACAT1 and -2; microsomal triglyceride transfer protein (MTP) inhibitors; probucol; niacin; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ) agonists including the compounds commonly referred to as glitazones for example troglitazone, pioglitazone and rosiglitazone and, including those compounds included within the structural class known as thiazolidinediones as well as those PPARγ agonists outside the thiazolidinedione structural class; PPARα agonists such as clofibrate, fenofibrate including micronized fenofibrate and gemfibrozil; PPAR dual α/γ agonists such as muraglitazar; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan and losartan with hydrochlorothiazide; angiotensin converting enzyme inhibitors such as enalapril and captopril; calcium channel blockers such as nifedipine and diltiazam; endothelian antagonists; agents that enhance ABC1 gene expression; FXR and LXR ligands including both inhibitors and agonists; bisphosphonate compounds such as alendronate sodium; and cyclooxygenase-2 inhibitors such as rofecoxib, etoricoxib and celecoxib. Anti-obesity agents can be employed in combination with a compound of this invention including, but not limited to, sibutramine, orlistat, topiramate, naltrexone, bupriopion, phentermine, and phentermine/topiramate combination (QNEXA®); NPY5 antagonists; Acetyl-CoA Carboxylase-1 and -2 (ACC) inhibitors; MCH1R antagonists; and CB1 antagonists/inverse agonists such as those described in WO03/077847 and WO05/000809. Additional anti-diabetes agents which may be employed in combination with a compound of this invention include but are not limited to DPP-4 (dipeptidylpeptidase-4) inhibitors such as sitagliptin (JANUVIA®) and vildagliptin (GALVUS®); sulfonylureas e.g., chlorpropamide, tolazamide, glyburide, glipizide, and glimepiride; biguanides, e.g., metformin; alpha-glucosidase inhibitors e.g., acarbose and miglitol; meglitinides e.g., repaglinide; glucagon-receptor antagonists; and glucokinase activators.

Example 1

Step A: A process for making Compound I is described in Example 7 of WO2006/099735. A 50 mg/ml Compound I stock solution was prepared by dissolving 1250 mg of Compound I free-base in 25 ml of methanol. 200 uL of the Compound I stock solution was dispensed to each well in a 96-well plate, resulting in 10 mg (0.02158 mmol) of Compound I per well. Next, a different acid was dispensed to each of columns 1-5, 7-9 and 11 on the masterplate. To form the salts, The acids were manually transferred as 0.1M acid stock solutions to each well in columns as indicated below (with the exception of HBr, HCl, and acetic acid in columns 6, 10, and 12 respectively, which were added after the GeneVac step described below). 216 uL of the 0.1M acid stock solution was added per well on the 96-well masterplate, resulting in a 1:1 mole ratio of acid to Compound I. Next the 96-well plate was placed in the GeneVac (centrifugal evaporator) to evaporate the solvents. HCl, HBr, and acetic acid were added to columns 10, 6 and 12 respectively, as 1M solutions (1M HCl in diethyl ether, 1M HBr in MeOH, and 1M acetic acid in MeOH, respectively), after the GeneVac step to prevent the acids from being removed in the centrifugal evaporator. The plate was evaporated for 2.5 hours at 1800 rpm, 35° C., under 2-6 mbar vacuum until dry. The 96-well plate was mapped by columns (acids) and rows (solvents-see Step B below). The acid and solvent mapping of the 96-well plate was as follows:

| Acids (columns): | Crystallization Solvent Composition (800 ul/well) |
|---|---|
| Column 1: Lactic acid | Row A: Ethanol |
| Column 2: Phosphoric Acid | Row B: 2-Propanol |
| Column 3: Sulfuric Acid | Row C: 1,2-Dichloroethane |
| Column 4: Ethanesulfonic acid | Row D: Toluene |
| Column 5: Succinic Acid | Row E: Isopropyl Acetate |
| Column 6: HBr | Row F: Nitromethane |
| Column 7: L-Tartaric Acid | Row G: Acetonitrile |
| Column 8: Methanesulfonic acid | Row H: 1,2-Dimethoxyethane |
| Column 9: p-Toluenesulfonic acid | |
| Column 10: HCl | |
| Column 11: Benzenesulfonic acid | |
| Column 12: Acetic Acid | |

Step B: Addition of crystallization solvents: The crystallization solvents (described above for Rows A-H) were dispensed (800 uL/well) to the masterplate from Step A. The 96-well plate was capped and placed on the deck of a Cavro robot to equilibrate for 3 hours while stirring at 30° C. While warm, the master plate was manually sampled into two crystallization plates (Cooling 285 uL, and Evaporation 300 uL). The cooling plate was cooled with a cubic cool down temperature profile from 65-10° C. over 10 hours. The cooling plate was equilibrated at 10° C. for 2 hours and then warmed to 20° C. for analysis. The evaporation plate was left uncapped in a hood overnight to allow evaporation of the solvents. The following day, each experiment was wicked to remove the remaining solvent and the plates were removed for analysis. The possible leads from the two studies (evaporative and cooling) were identified by XRPD and cross-polarized light microscopy. Four possible different crystalline leads were identified in the initial acid salt screen as containing crystalline material by XRPD with noticeable differences in the diffractograms with respect to the starting freebase and the bulk acids. These four crystalline leads were selected for scale-up experiments as described in Example 2.

Example 2

Scale-Up Preparation of p-Toluenesulfonic Acid, Benzenesulfonic acid and Acetic Acid salts of Compound I 1000 uL of the 50 mg/ml stock solution of Compound I free base (0.1079 mmol) was added into each of ten 4-mL scale-up reaction vials. Following the Compound I free base stock solution dispense, 1 mole equivalent (0.1079 mmol) of acid was added to each scale-up experiment. The scale-up experiments were then placed into the GeneVac to evaporate off the additional solvents. The crystallization solvents were manually dispensed to each scale-up experiment (2 mL total solvent volume per vial). See Table 1 for complete composition of the scale-up experiments. The cooling scale-up experiments were capped and placed in a 65° C. Torrey Pines oven to equilibrate for 3 hours.

The cooling scale-up experiments (vials A1 and A2) were cooled with a cubic cool down temperature profile from 65-10° C. over 10 hours. The cooling scale-up experiments were equilibrated at 10° C. for 2 hours and then warmed to 20° C. The cooling scale-up experiment (A2) was removed from the oven and no solids were observed. This scale-up experiment was then uncapped and allowed to concentrate at ambient temperature in an attempt to induce crystallization. The evaporative scale-up experiments (vials A3 and A4) were uncapped, and allowed to concentrate at ambient temperature. The isolated solids from scale-up experiments were analyzed under a cross-polarized light microscope, and by thermogravimetry analysis (TGA), DSC, and by XRPD.

TABLE 1

| Experiment/ Vial | Study | Acid | Crystallization Solvent |
|---|---|---|---|
| A1 | Cooling | p-toluenesulfonic acid | 1,2-dichlorethane |
| A2 | Cooling | Benzenesulfonic acid | 1,2-dichlorethane |
| A3 | Evaporation | p-toluenesulfonic acid | acetonitrile |
| A4 | Evaporation | Acetic Acid | acetonitrile |

Experiment A4 generated the acetic acid salt of Compound I as an amorphous gel. Experiments A1 and A3 generated a crystalline tosylate salt of Compound I. The isolated solids from Experiment A1 showed a gradual weight loss of 0.61 wt % (possibly due to the loss of residual solvent) occurring between 23.4° C. and 179.7° C. and decomposition after 180.0° C. by TGA. The differential scanning calorimetry (DSC) curve shows a single sharp endotherm (melt) which has an onset at 162.9° C. and a peak max at 166.0° C. By proton NMR, the isolated solid appears to contain a 1:1 mixture of p-toluenesulfonic acid:Compound I.

Experiment A2 generated a crystalline besylate salt of Compound I. The X-ray powder diffractogram (XRPD) of the isolated solids from Experiment A2 is shown in Figure #. This material shows a gradual weight loss of 4.3 wt % (possibly due to the loss of residual solvent) occurring between 19.8° C. and 199.4° C. and decomposition after 200.0° C. by TGA. The DSC curve shows a single small endotherm which has an onset at 62.5° C. and a peak max at 64.9° C. A thermal event or step which occurred at 144.8° C. was also observed on the DSC. By proton NMR, the isolated solid appears to contain a 1:1 mixture of benzenesulfonic acid:Compound I.

Example 3

Preparation of p-toluenesulfonic acid and benzenesulfonic acid salts of (S)-4-(4-fluorophenyl)-7-[({5-[1-hydroxy-1-(trifluoromethyl)propyl]-1,3,4-oxadiazol-2-yl}amino)methyl]-2H-chromen-2-one Benzenesulfonic acid salt: Solid Compound 1 (400 mg, 0.86 mmol) was dissolved in 1,2-dichloroethane (4 mL). A solution of benzenesulfonic acid hydrate (137 mg, 0.86 mmol) in 1,2-dichloroethane (5 mL) was added. Hexane (1 mL) was added and a precipitate began forming. The slurry was stirred for 15 min, concentrated, suspended in hexane (30 mL) and filtered. The solids were washed with hexane (30 mL) and dried on the frit to afford Compound I besylate salt as a grayish-white solid, 454 mg. The solid was recrystallized from 2-propanol/hexane to afford an off-white solid.

p-Toluenesulfonic acid salt: Solid Compound 1 (400 mg, 0.86 mmol) was dissolved in 1,2-dichloroethane (5 mL). Solid p-toluenesulfonic acid monohydrate (164 mg) was added and the mixture was heated at 70° C. for 5 min for complete dissolution. The solution was cooled to room temperature and hexane (2 mL) was added. The slurry was filtered and washed with hexane (30 mL) and dried on the frit to afford Compound I tosylate as a white solid, 450 mg.

Example 4

Preparation of p-Toluenesulfonic Acid salt of (S)-4-(4-fluorophenyl)-7-[({5-[1-hydroxy-1-(trifluoromethyl)propyl]-1,3,4-oxadiazol-2-yl}amino)methyl]-2H-chromen-2-one

| Materials | MW | Amount | mMoles |
|---|---|---|---|
| Compound I | 463.38 | 5.291 g | 11.418 |
| p-Toluene sulfonic acid monohydrate (TsOH) | 190.22 | 2.172 g | 11.418 |
| iso-Propyl acetate | 102.13 (d 0.874) | 66 mL (12.5 mL/g) | |

To a 100 mL round bottom flask containing a crude solution of Compound I (5.4 g) in about 15.5 mL iPAc was added iPAc (40 mL) and the mixture was stirred at rt for 16 h. Stirring was stopped and the precipitated solids were removed by decantation. Assay of the supernatant indicated 5.2 g of Compound I p-Toluene sulfonic acid monohydrate (2.172 g, 11.418 mmol) was charged to iPAc (13.2 mL) and the suspension was warmed to 60° C. and stirred until complete dissolution of TsOH (approx 5 min). To the hot TsOH solution (~60° C.) in iPAc the solution of Compound I was added over 2 h. After ~20% of free base solution was added addition was stopped. Seed (1 mg Compound I tosylate salt) were added and the mixture was stirred for 10 min. Addition of free base was then continued. After the end of the addition, the batch was gradually cooled to room temperature over 2 h and let stir at room temperature for 16 h. The agitation was stopped and the batch was filtered. The filter cake was suspended in iPAc (40 mL), filtered, re-suspended in iPAc (40 mL) and filtered. The solids were then transferred to a vacuum oven at 30° C. and dried for 18 h to obtain the title compound.

Example 5

Crystallization of Compound I Tosylate Salt (Basis 1.00 mole (463.38 g) of Compound I in a solution of 10-11.5 volumes (4634-5329 mL) of Isopropyl Acetate)

p-Toluenesulfonic acid monohydrate (p-TSA, 1.00 mole, 190.22 g) is dissolved in 1158 mL of isopropyl acetate (IPAc). The slurry is heated to 57-60° C. to dissolve the pTSA and aged for 30 minutes. Dissolution is confirmed by visual inspection of a sample of the mixture. The mixture is filtered hot (57-60° C.) and follow flushed with 463 mL of 57-60° C. isopropyl acetate.

To supersaturate the batch, 25% of a solution of Compound I in IPAc (typically approx. 10.7 wt %) is combined with the pTSA/IPAc mixture at 57-60° C. Neat IPAc is charged to the vessel to achieve a target of 9-10 wt % Compound I tosylate salt. The batch is seeded with 4.6 grams (1 wt % based on Compound I) of the tosylate salt and the seed bed is aged for 30 minutes at 57-60° C. The remaining 75% of the solution of Compound I in IPAc is charged to the batch over 2-3 hours, maintaining the batch temperature at 57-60° C. A controlled cooldown of the batch to 20-25° C. over three hours is performed followed by a 2 hour age at 15-25° C. The slurry is then wet milled at 15-20° C. until steady state particle size is achieved. An optional heat/cool cycle can be performed for the dissolution of fines. The heat/cool cycle consists of heating the batch to 57-60° C., aging for 15 minutes and then cooling to 20° C. over 3 hours. After aging the batch for at least 2 hours at 15-20° C., the batch is filtered. Two displacement washes of the cake with 1854 mL of isopropyl acetate are performed. A third displacement wash with 1390 mL of isopropyl acetate is charged directly to the filter. The cake is dried with vacuum and a nitrogen sweep at 55-60° C. until <0.5 wt % IPAc. The batch is then co-milled and blended.

Example 6

Crystallization of Compound I Tosylate Salt (Alternate Procedure)

(Basis 0.0344 mole (15.96 assay g) of Compound I in a solution of 13.5-15.4 volumes (216-246 mL) of isopropyl acetate)

To the seed vessel is charged 57.8 mL IPAc followed by 0.289 g of wet milled Compound I tosylate salt to saturate the solution. The mixture is heated to 57-60° C. and then 1.59 g of wet milled Compound I tosylate salt (10 wt % seed based on Compound I) is added to the vessel. In a separate vessel, 0.0344 mole of p-toluenesulfonic acid mono-hydrate (6.55 g) is dissolved in 84 mL of isopropyl acetate. The slurry is heated to 57-60° C. to dissolve the pTSA and aged for 30 minutes. Dissolution is confirmed by visual inspection of a sample of the mixture. The pTSA solution is then cooled to 15-25° C. The pTSA solution and a solution of Compound I in IPAc (0.0344 mole, 15.96 assay g in 216-246 mL of IPAc) are then added simultaneously to the seed vessel over 10 hours, maintaining the crystallization vessel at 57-60° C. A controlled cooldown of the batch to 15-25° C. over three hours is performed followed by a 2 hour age at 15-25° C. The batch is then filtered. Two displacement washes of the cake with 63.8 mL of isopropyl acetate are performed. The cake is dried with vacuum and a nitrogen sweep at 55-60° C. until <0.5 wt % IPAc. The batch is then co-milled and blended.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the active agent used in the instant invention as indicated above. It is intended, therefore, that the invention be defined by the scope of the claims which follow and that such claims be interpreted as broadly as is reasonable.

What is claimed is:

1. Crystalline p-toluenesulfonic acid salt of (−)4-(4-fluorophenyl)-7-[({5-[1-hydroxy-1-(trifluoromethyl)propyl]-1,3,4-oxadiazol-2-yl}amino)methyl]-2H-chromen-2-one characterized by having an XRPD pattern obtained using CuKα radiation containing at least one d-spacing selected from 17.77, 8.90 and 5.17.

2. Crystalline p-toluenesulfonic acid salt of (−)4-(4-fluorophenyl)-7-[({5-[1-hydroxy-1-(trifluoromethyl)propyl]-1,3,4-oxadiazol-2-yl}amino)methyl]-2H-chromen-2-one characterized by having at least one chemical shift value obtained by solid-state carbon-13 CPMAS NMR selected from the group consisting of 48.5, 124.1, 152.4, 28.4, 141.3, 162.1, 74.8, 154.4 and 164.5 parts per million.

3. Crystalline p-toluenesulfonic acid salt of (−)4-(4-fluorophenyl)-7-[({5-[1-hydroxy-1-(trifluoromethyl)propyl]-1,3,4-oxadiazol-2-yl}amino)methyl]-2H-chromen-2-one characterized by having at least two chemical shift values obtained by solid-state carbon-13 CPMAS NMR selected from the group consisting of 48.5, 124.1, 152.4, 28.4, 141.3, 162.1, 74.8, 154.4 and 164.5 parts per million.

4. Crystalline p-toluenesulfonic acid salt of (−)4-(4-fluorophenyl)-7-[({5-[1-hydroxy-1-(trifluoromethyl)propyl]-1,3,4-oxadiazol-2-yl}amino)methyl]-2H-chromen-2-one characterized by having at least one chemical shift value obtained by solid-state fluorine-19 CPMAS NMR selected from the group consisting of −50.2, −75.6 and −101.3.

5. Crystalline p-toluenesulfonic acid salt of (−)4-(4-fluorophenyl)-7-[({5-[1-hydroxy-1-(trifluoromethyl)propyl]-1,3,4-oxadiazol-2-yl}amino)methyl]-2H-chromen-2-one characterized by having at least two chemical shift values obtained by solid-state fluorine-19 CPMAS NMR selected from the group consisting of −50.2, −75.6 and −101.3.

6. A pharmaceutical composition comprising a crystalline p-toluenesulfonic acid salt selected from the group consisting of:

(a) a salt characterized by having at least one chemical shift value obtained by solid-state carbon-13 CPMAS NMR selected from the group consisting of 48.5, 124.1, 152.4, 28.4, 141.3, 162.1, 74.8, 154.4 and 164.5 parts per million;

(b) a salt characterized by having at least two chemical shift values obtained by solid-state carbon-13 CPMAS NMR selected from the group consisting of 48.5, 124.1, 152.4, 28.4, 141.3, 162.1, 74.8, 154.4 and 164.5 parts per million;

(c) a salt characterized by having at least one chemical shift value obtained by solid-state fluorine-19 CPMAS NMR selected from the group consisting of −50.2, −75.6 and −101.3; and (d) a salt characterized by having at least two chemical shift values obtained by solid-state fluorine-19 CPMAS NMR selected from the group consisting of −50.2, −75.6 and −101.3;

and a pharmaceutically acceptable carrier.

* * * * *